United States Patent
Adami et al.

(10) Patent No.: US 12,311,055 B2
(45) Date of Patent: *May 27, 2025

(54) COMPOSITIONS AND METHODS FOR NANOPARTICLE LYOPHILE FORMS

(71) Applicant: Nitto Denko Corporation, Osaka (JP)

(72) Inventors: Roger Adami, Carlsbad, CA (US);
Yuwei Wang, Oceanside, CA (US);
Haiqing Yin, San Marcos, CA (US);
Liping Wang, Carlsbad, CA (US);
Dong Liu, Irvine, CA (US); Wenbin Ying, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/346,115

(22) Filed: Jun. 30, 2023

(65) Prior Publication Data

US 2024/0000710 A1    Jan. 4, 2024

Related U.S. Application Data

(60) Continuation of application No. 16/377,032, filed on Apr. 5, 2019, now Pat. No. 11,737,982, which is a division of application No. 15/217,098, filed on Jul. 22, 2016, now Pat. No. 10,300,018.

(60) Provisional application No. 62/195,356, filed on Jul. 22, 2015.

(51) Int. Cl.

| | |
|---|---|
| A61K 9/16 | (2006.01) |
| A61K 9/1271 | (2025.01) |
| A61K 9/14 | (2006.01) |
| A61K 9/19 | (2006.01) |
| A61K 9/51 | (2006.01) |
| A61K 31/713 | (2006.01) |
| A61K 47/26 | (2006.01) |
| A61K 47/36 | (2006.01) |
| A61K 47/40 | (2006.01) |
| C12N 15/11 | (2006.01) |
| C12N 15/113 | (2010.01) |

(52) U.S. Cl.
CPC ............ *A61K 9/19* (2013.01); *A61K 9/1271* (2013.01); *A61K 9/145* (2013.01); *A61K 9/146* (2013.01); *A61K 9/5123* (2013.01); *A61K 31/713* (2013.01); *A61K 47/26* (2013.01); *A61K 47/36* (2013.01); *A61K 47/40* (2013.01); *C12N 15/111* (2013.01); *C12N 15/113* (2013.01); *C12N 2310/14* (2013.01); *C12N 2320/32* (2013.01)

(58) Field of Classification Search
CPC ............................... A61K 9/16; A61K 9/1688
See application file for complete search history.

(56) References Cited

U.S. PATENT DOCUMENTS

| | | | |
|---|---|---|---|
| 4,537,683 A | 8/1985 | Isacoff | |
| 4,537,883 A | 8/1985 | Alexander | |
| 4,927,571 A | 5/1990 | Huang | |
| 8,748,397 B2 | 6/2014 | Cesca-Cancian | |
| 11,737,982 B2* | 8/2023 | Adami ................ | A61K 9/5123 424/489 |
| 2004/0121983 A1 | 6/2004 | Chattopadhyay | |
| 2005/0002998 A1 | 1/2005 | Chang | |
| 2010/0278885 A1 | 11/2010 | Ikeda | |
| 2011/0237686 A1* | 9/2011 | Ng ...................... | A61K 9/5146 264/28 |
| 2011/0275704 A1* | 11/2011 | Troiano ................ | A61K 47/34 977/773 |
| 2013/0022665 A1 | 1/2013 | Niitsu | |
| 2013/0115274 A1 | 5/2013 | Knopov et al. | |
| 2013/0315987 A1 | 11/2013 | Lu | |
| 2014/0255475 A1 | 9/2014 | Cabral-Lilly | |
| 2014/0288023 A1 | 9/2014 | Cheng | |
| 2014/0288160 A1 | 9/2014 | Guild et al. | |
| 2015/0086613 A1 | 3/2015 | De Rosa et al. | |

FOREIGN PATENT DOCUMENTS

| | | |
|---|---|---|
| CN | 103748078 A | 4/2014 |
| JP | 2008-520600 | 6/2008 |
| JP | 2015-502345 | 1/2015 |
| WO | WO 2006/050327 | 5/2006 |
| WO | WO 2006/053646 | 5/2006 |
| WO | WO 2011/103150 | 8/2011 |
| WO | WO 2012/170889 | 12/2012 |
| WO | WO 2013/093648 | 6/2013 |
| WO | WO 2014/145839 | 9/2014 |

OTHER PUBLICATIONS

Office Action issued in U.S. Appl. No. 15/217,098, dated Mar. 12, 2018, filed Jul. 22, 2016.
Office Action issued in U.S. Appl. No. 16/377,032, dated May 15, 2020, filed Apr. 5, 2019.
Office Action issued in U.S. Appl. No. 16/377,032, dated Nov. 13, 2020, filed Apr. 5, 2019.
Office Action issued in U.S. Appl. No. 16/377,032, dated Oct. 6, 2021, filed Apr. 5, 2019.

(Continued)

*Primary Examiner* — Micah Paul Young
(74) *Attorney, Agent, or Firm* — Knobbe, Martens, Olson & Bear, LLP

(57) ABSTRACT

Compositions for making a solid lyophile of one or more nucleic acid active agents, which can be reconstituted as a drug product. The composition can include an aqueous suspension of lipid nanoparticles in a pharmaceutically acceptable solution, wherein the lipid nanoparticles encapsulate one or more nucleic acid active agents, a dextrin compound, and a saccharide compound. The nucleic acid active agents can be RNAi molecules capable of mediating RNA interference, as well as other RNAs and oligonucleotides.

19 Claims, 2 Drawing Sheets

(56) References Cited

OTHER PUBLICATIONS

Office Action issued in U.S. Appl. No. 16/377,032, dated Mar. 17, 2022, filed Apr. 5, 2019.
Office Action issued in U.S. Appl. No. 16/377,032, dated Jun. 22, 2022, filed Apr. 5, 2019.
Office Action issued in U.S. Appl. No. 16/377,032, dated Oct. 6, 2022, filed Apr. 5, 2019.
Notice of Preliminary Rejection dated Jun. 19, 2023 for Korean Application No. 10-2018-7005141.
Abdelwahed, Wassim, et al., "Freeze-drying of nanoparticles: Formulation, process and storage considerations", Advanced Drug Delivery Reviews, vol. 58, Issue 15, 2006, pp. 1688-1713.
Gould, "2-Hydroxypropyl-b-cyclodextrin (HP-b-CD): A toxicology review," 2005, Food and Chemical Toxicology, vol. 13, pp. 1451-1459.
Extended European Search Report issued on Feb. 1, 2019 for the European Patent Application No. 16828602.09.
Eurasian Office Action dated Dec. 10, 2018 for Eurasian Application No. 201890367/28.
Office Action issued in Eurasian Patent Application No. 201890367/28 dated Jul. 10, 2019.
Office Action issued in Mexican Application No. MX/a/2018/000891 dated Nov. 5, 2019.
Office Action issued in Indian Application No. 201847005858 dated Mar. 6, 2020.
First Office Action issued in Japanese Application 2018-503253 dated May 15, 2020.
Office Action issued in Israel Patent Application No. 257029.
Office Action issued in Brazilian Patent Application No. BR112018001178-9 on Aug. 4, 2020.
Office Action issued in Chinese Patent Application No. 201680054543.9, dated Jul. 30, 2020.
Office Action issued in Japanese Application No. 2018-503253 dated Sep. 30, 2020.
Office Action issued in Australian Application No. 2016297153 dated Nov. 23, 2020.
Office Action issued in Chinese Patent Application No. 201680054543.9 dated Jan. 7, 2021.
Office Action issued in Chinese Patent Application No. 105123227 dated Feb. 8, 2021.
Hearing Notice issued in Indian Application No. 2018-47005858 dated Mar. 23, 2021.
Office Action received in Canadian Patent Application No. 2,992,849 issued Mar. 31, 2022.
Office Action received in Japanese Patent Application No. 2021-072339 issued Mar. 31, 2022.
Office Action issued in Israeli Application No. 288342, dated Jun. 30, 2022.
Office Action issued in Chinese Application No. 202110916430.8, dated Oct. 10, 2022.
Decision of Refusal issued in Japanese Application No. 2021-072339, dated Nov. 15, 2022.

\* cited by examiner

COMPOSITIONS AND METHODS FOR NANOPARTICLE LYOPHILE FORMS

RELATED APPLICATIONS

Any and all applications for which a domestic priority claim is identified in the Application Data Sheet as filed with the present application are hereby incorporated by reference under 37 CFR 1.57. This application is continuation of U.S. patent application Ser. No. 16/377,032, filed Apr. 5, 2019, which is a divisional of U.S. patent application Ser. No. 15/217,098, filed Jul. 22, 2016, now U.S. Pat. No. 10,300,018, which claims priority to U.S. Provisional Patent Application No. 62/195,356, filed Jul. 22, 2015, entitled COMPOSITIONS AND METHODS FOR NANOPARTICLE LYOPHILE FORMS, the contents of each application is herein incorporated by reference in their entireties.

BACKGROUND OF THE INVENTION

Therapeutics based on nucleic acid compounds include various RNA forms such as siRNAs, antisense RNA, microRNAs, as well as various forms of DNAs and plasmids, hybrid oligonucleotides, and aptamers, among others.

Transfection of nucleic acid therapeutics and other agents has been accomplished by encapsulating the active molecules in lipid nanoparticles. Drawbacks of this methodology include the inability to store compositions for later use because of degradation of the nanoparticles or their encapsulated cargo. For example, compositions of lipid nanoparticles that encapsulate siRNA molecules may be stable for only a few minutes or hours at 25° C., and only a few days or weeks at 4° C. Further drawbacks include the need for very low temperature storage of the lipid nanoparticle compositions.

One way to provide for long-term storage of a therapeutic composition is to prepare a lyophile form, which can be stored and reconstituted to provide a formulation for administration of the therapeutic.

However, it has not been possible in general to generate lyophile forms of lipid nanoparticles containing nucleic acid agents, so that the lipid nanoparticle can be regenerated with the nucleic acid agent encapsulated to form a stable formulation. The lyophilization process can destroy the nanoparticles and/or the nucleic acid agents. Some methods have involved chemically attaching protective groups or components to the lipid nanoparticles, or to the nucleic acid agent, which is disadvantageous. Other methods may use liposomes as an adjuvant, without providing for encapsulation of the nucleic acid agents.

There is a continuing need for compositions and methods to provide lyophile forms of nanoparticles that can be reconstituted with favorable properties, including transfection activity, particle size, storage time, and serum stability to deliver various nucleic acid agents.

What is needed are compositions and compounds for forming stable solutions or suspensions of lipid nanoparticles that can be stored in solid lyophile forms, where the nanoparticles encapsulate nucleic acid agents.

BRIEF SUMMARY

This invention relates to the fields of biopharmaceuticals and therapeutics composed of nucleic acid based molecules. More particularly, this invention relates to methods and compositions for lyophile forms of nucleic acid therapeutic compositions.

This invention provides methods and compositions for therapeutics composed of nucleic acid based molecules. More particularly, this invention provides methods and compositions for lyophile forms of nucleic acid based therapeutic compositions.

This invention further provides lyophile forms of nanoparticles that can be reconstituted into effective therapeutic compositions, which can be used to deliver therapeutic nucleic acid agents for transfection.

In some aspects, this invention provides compositions and compounds for forming solutions or suspensions of therapeutic lipid nanoparticles that are stable in lyophilization processes. The therapeutic lipid nanoparticles can encapsulate nucleic acid agents, and can be transformed and stored in solid lyophile forms. The lyophile forms can be reconstituted to provide therapeutic lipid nanoparticles with encapsulated nucleic acid agents. The reconstituted lipid nanoparticles can have surprisingly advantageous transfection properties, including particle size and distribution.

Embodiments of this invention include a range of compositions and compounds for forming solutions or suspensions of therapeutic lipid nanoparticles that can undergo a lyophilization process to provide stable, solid lyophile forms for long-term storage of a nucleic acid therapeutic.

Embodiments of this invention include the following:

A composition for making a solid lyophile of lipid nanoparticles comprising one or more nucleic acid active agents, the composition comprising:
  an aqueous suspension of the lipid nanoparticles in a pharmaceutically acceptable solution, wherein the lipid nanoparticles encapsulate the one or more nucleic acid active agents;
  a dextrin compound; and
  a saccharide sugar compound.

The composition above, wherein the total amount of the dextrin and sugar compounds is from 2% to 20% (w/v) of the composition.

The composition above, wherein the dextrin compound is from 40% to 70% (w/v) of the total amount of the dextrin and sugar compounds.

The composition above, wherein the dextrin compound is from 40% to 55% (w/v) of the total amount of the dextrin and sugar compounds.

The composition above, wherein the dextrin compound is 40% to 45% (w/v) of the total amount of the dextrin and sugar compounds.

The composition above, wherein upon lyophilization and reconstitution of the composition, the average size of the nanoparticles is within 10% of their size in the original composition.

The composition above, wherein upon lyophilization, storage and reconstitution of the composition, the average size of the nanoparticles is within 10% of their size in the original composition.

The composition above, wherein the lyophilized composition is stored at 5° C. for at least one month.

The composition above, wherein the lyophilized composition is stored at −20° C. for at least one month.

The composition above, wherein the nanoparticles have an average diameter of from 45 nm to 110 nm.

The composition above, wherein the concentration of the nucleic acid active agents is from 1 mg/mL to 10 mg/mL, or from 3 mg/mL to 5 mg/mL.

The composition above, wherein the one or more nucleic acid active agents are RNAi molecules capable of mediating RNA interference. The composition above, wherein the RNAi molecules are siRNAs, shRNAs, ddRNAs, piRNAs, or rasiRNAs.

The composition above, wherein the one or more nucleic acid active agents are miRNAs, antisense RNAs, plasmids, hybrid oligonucleotides, or aptamers.

The composition above, wherein the pharmaceutically acceptable solution is a HEPES buffer, a phosphate buffer, a citrate buffer, or a buffer containing Tris(hydroxymethyl) aminomethane.

The composition above, wherein the dextrin compound is a cyclodextrin.

The composition above, wherein the cyclodextrin compound has one or more of the 2, 3 and 6 hydroxyl positions substituted with sulfoalkyl, benzenesulfoalkyl, acetoalkyl, hydroxyalkyl, hydroxyalkyl succinate, hydroxyalkyl malonate, hydroxyalkyl glutarate, hydroxyalkyl adipate, hydroxyalkyl, hydroxyalkyl maleate, hydroxyalkyl oxalate, hydroxyalkyl fumarate, hydroxyalkyl citrate, hydroxyalkyl tartrate, hydroxyalkyl malate, or hydroxyalkyl citraconate groups.

The composition above, wherein the cyclodextrin compound is (2-hydroxypropyl)-β-cyclodextrin, 2-hydroxypropyl-β-cyclodextrin succinate, (2-hydroxypropyl)-γ-cyclodextrin, or 2-hydroxypropyl-γ-cyclodextrin succinate.

The composition above, wherein the cyclodextrin compound is sulfobutyl ether β-cyclodextrin or sulfobutyl ether γ-cyclodextrin.

The composition above, wherein the cyclodextrin compound is methyl-β-cyclodextrin or methyl-γ-cyclodextrin.

The composition above, wherein the cyclodextrin compound is attached to a polymer chain or network.

The composition above, wherein the cyclodextrin compound includes an adsorbate compound.

The composition above, wherein the adsorbate compound is selected from cholesterol, lanosterol, zymosterol, zymostenol, desmosterol, stigmastanol, dihydrolanosterol, 7-dehydrocholesterol, pegylated cholesterol, cholesteryl acetate, cholesteryl arachidonate, cholesteryl butyrate, cholesteryl hexanoate, cholesteryl myristate, cholesteryl palmitate, cholesteryl behenate, cholesteryl stearate, cholesteryl caprylate, cholesteryl n-decanoate, cholesteryl dodecanoate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, cholesteryl linoleate, beta-sitosterol, campesterol, ergosterol, brassicasterol, delta-7-stigmasterol, and delta-7-avenasterol.

The composition above, wherein the saccharide sugar compound is a monosaccharide or disaccharide sugar compound.

The composition above, wherein the sugar compound is selected from sucrose, lactose, lactulose, maltose, trehalose, cellobiose, kojibiose, sakebiose, isomaltose, sophorose, laminaribiose, gentiobiose, turanose, maltulose, isomaltulose, gentiobiulose, mannobiose, melibiose, melibiulose, and xylobiose.

A process for making a solid lyophile of one or more nucleic acid active agents, the process comprising lyophilizing a composition described above. This invention further contemplates a solid lyophile made by the process above, as well as a drug product made by reconstituting a solid lyophile above.

This invention further includes a process for making a nucleic acid drug product, the process comprising:
   synthesizing lipid nanoparticles, wherein the lipid nanoparticles encapsulate one or more nucleic acid active agents;
   providing an aqueous suspension of the lipid nanoparticles in a pharmaceutically acceptable solution;
   adding a dextrin compound to the solution containing the lipid nanoparticles;
   adding a saccharide sugar compound to the solution containing the lipid nanoparticles;
   lyophilizing the solution containing the lipid nanoparticles, thereby forming a solid lyophile;
   reconstituting the lyophile in a pharmaceutically acceptable carrier, thereby forming a nucleic acid drug product.

The process above, wherein the total amount of the dextrin and saccharide sugar compounds is from 2% to 20% (w/v) of the solution containing the lipid nanoparticles.

The process above, wherein the dextrin compound is from 40% to 70% (w/v) of the total amount of the dextrin and saccharide sugar compounds.

The process above, wherein the dextrin compound is from 40% to 55% (w/v) of the total amount of the dextrin and saccharide sugar compounds.

The process above, wherein the dextrin compound is 40% to 45% (w/v) of the total amount of the dextrin and saccharide sugar compounds.

The process above, wherein upon reconstitution, the average size of the nanoparticles is within 10% of their size when synthesized.

The process above, further comprising storing the lyophile before reconstitution.

The process above, wherein upon storage and reconstitution of the lyophile, the average size of the nanoparticles is within 10% of their size when synthesized.

The process above, wherein the lyophile is stored at 5° C. for at least one month.

The process above, wherein the lyophile is stored at −20° C. for at least one month.

The process above, wherein the nanoparticles have an average diameter of from 45 nm to 110 nm.

The process above, wherein the concentration of the nucleic acid active agents is from 1 mg/mL to 10 mg/mL.

The process above, wherein the one or more nucleic acid active agents are RNAi molecules capable of mediating RNA interference. The process above, wherein the RNAi molecules are siRNAs, shRNAs, ddRNAs, piRNAs, or rasiRNAs.

The process above, wherein the one or more nucleic acid active agents are miRNAs, antisense RNAs, plasmids, hybrid oligonucleotides, or aptamers.

The process above, wherein the pharmaceutically acceptable carrier is sterile water, water for injection, sterile normal saline, bacteriostatic water for injection, or a nebulizer solution.

The process above, wherein the pharmaceutically acceptable carrier is a pharmaceutically acceptable solution.

The process above, wherein the pharmaceutically acceptable solution is a HEPES buffer, a phosphate buffer, a citrate buffer, or a buffer containing Tris(hydroxymethyl)aminomethane.

The process above, wherein the dextrin compound is a cyclodextrin.

The process above, wherein the cyclodextrin compound has one or more of the 2, 3 and 6 hydroxyl positions substituted with sulfoalkyl, benzenesulfoalkyl, acetoalkyl, hydroxyalkyl, hydroxyalkyl succinate, hydroxyalkyl malonate, hydroxyalkyl glutarate, hydroxyalkyl adipate, hydroxyalkyl, hydroxyalkyl maleate, hydroxyalkyl oxalate, hydroxyalkyl fumarate, hydroxyalkyl citrate, hydroxyalkyl tartrate, hydroxyalkyl malate, or hydroxyalkyl citraconate groups.

The process above, wherein the cyclodextrin compound is (2-hydroxypropyl)-β-cyclodextrin, 2-hydroxypropyl-β-cyclodextrin succinate, (2-hydroxypropyl)-γ-cyclodextrin, or 2-hydroxypropyl-γ-cyclodextrin succinate.

The process above, wherein the cyclodextrin compound is sulfobutyl ether β-cyclodextrin or sulfobutyl ether γ-cyclodextrin.

The process above, wherein the cyclodextrin compound is methyl-β-cyclodextrin or methyl-γ-cyclodextrin.

The process above, wherein the cyclodextrin compound includes an adsorbate compound.

The process above, wherein the saccharide sugar compound is a monosaccharide or disaccharide sugar compound.

The process above, wherein the pharmaceutically acceptable carrier is sterile water, water for injection, sterile normal saline, bacteriostatic water for injection, or a nebulizer solution.

The process above, wherein the pharmaceutically acceptable carrier is a pharmaceutically acceptable solution.

The process above, wherein the reconstituted nucleic acid drug product has less 0.001% (w/v) of aggregate particles with a size greater than 0.2 µm.

The process above, wherein the nucleic acid drug product is reconstituted in a time period of 3 to 30 seconds.

The process above, wherein the nucleic acid drug product is reconstituted after a storage time period of six months and retains 80% activity of the nucleic acid agents.

The process above, wherein the reconstituted nucleic acid drug product has less 0.001% (w/v) of aggregate particles with a size greater than 0.2 µm.

The process above, wherein the reconstituted nucleic acid drug product has reduced cytokine activation.

The process above, wherein the nucleic acid drug product is reconstituted in a time period of 3 to 30 seconds.

The process above, wherein the nucleic acid drug product is reconstituted after a storage time period of six months and retains 80% activity of the nucleic acid agents.

BRIEF DESCRIPTION OF THE DRAWINGS

As shown in FIG. 1, the reconstituted siRNA nanoparticle drug formulation exhibited profound and surprising potency for gene silencing of Hsp47 (GP46) in vivo. The in vivo potency is a rigorous test for the viability of lyophilized, reconstituted nanoparticles containing a nucleic acid agent. The nanoparticle formulation of the siRNA that was lyophilized included a total protectant content of 10% (w/v), which was composed of 40% (w/v) (2-hydroxypropyl)-β-cyclodextrin and 60% sucrose.

As shown in FIG. 2, the plasma concentration pharmacokinetics of the lyophilized, reconstituted siRNA drug formulation was essentially the same as a comparative control formulation that had only been frozen.

DETAILED DESCRIPTION OF THE INVENTION

Figure 1:
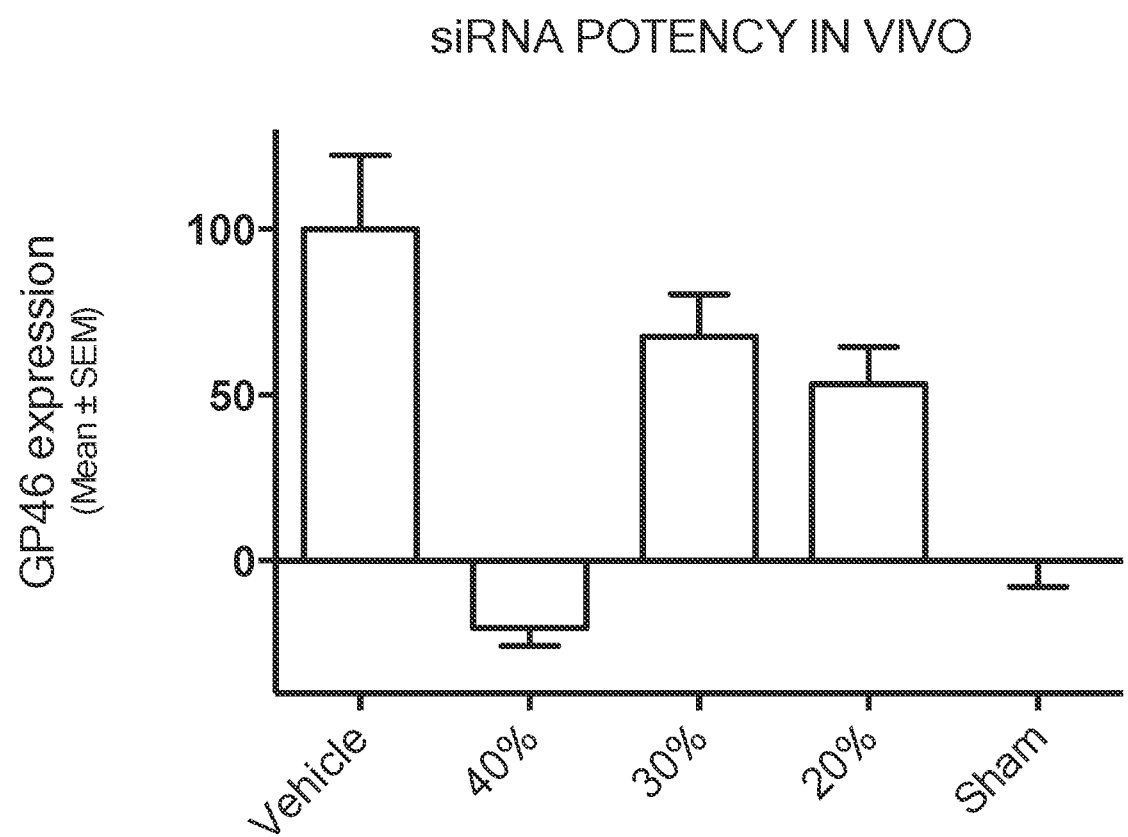
FIG. 1 shows experimental results for in vivo potency of a nucleic acid agent, which was a siRNA targeted to suppress Hsp47 (GP46), obtained with a final drug product that was a reconstituted solution of a solid, lyophilized nanoparticle formulation of the siRNA. Reconstituted siRNA drug formulations were used in a Dimethylnitrosamine (DMN) Induced Liver Fibrosis Rat Model.

This invention provides methods and compositions for therapeutics composed of nucleic acid based molecules. In some embodiments, this invention provides methods and compositions for making lyophile forms of therapeutic compositions containing nucleic acid agents.

In some aspects, this invention provides lyophile forms of nanoparticles that can be reconstituted into effective therapeutic compositions. The nanoparticles can encapsulate nucleic acid agents as cargo. The lyophile forms of this invention can be used to re-compose and deliver nanoparticle formulations encapsulating therapeutic nucleic acid agents for transfection.

In further aspects, this invention provides compounds and methods for forming solutions or suspensions of therapeutic lipid nanoparticles that are stable in lyophilization processes. The lyophilization processes of this invention can provide stable lyophile forms of therapeutic lipid nanoparticles, in which the nanoparticles can encapsulate nucleic acid agents. The lyophile forms can be stored for a period of time, and reconstituted to provide therapeutic lipid nanoparticles with encapsulated nucleic acid agents.

In some embodiments, this invention includes a range of compositions and compounds for solutions or suspensions of lipid nanoparticles that can undergo a lyophilization process to provide stable, solid lyophile forms for long-term storage of a nucleic acid therapeutic. Compositions and processes of this invention can provide lyophile forms that can be reconstituted and provide advantageous activity, particle size, storage time, and serum stability.

In further aspects, this invention relates to compounds, compositions and methods for providing nanoparticles to deliver and distribute active agents or drug compounds to subjects, tissues, and organs.

This invention provides a range of lipid compounds and ionizable compounds for delivering active agents to cells. The lipid compounds and ionizable compounds of this disclosure can be used to form nanoparticles to deliver and distribute active agents.

This invention contemplates lipid nanoparticle drug formulations containing, for example, siRNA agents, which can be prepared by lyophilization of a suspension of the nanoparticles, and reconstitution of the nanoparticles into a suspension.

In some embodiments, lipid nanoparticles can be synthesized by high speed injection of lipid/ethanol solution into an siRNA buffer solution. A second buffer can be diafiltered and used as an external buffer through TFF cartridges to make a final product aqueous suspension.

In some embodiments, the nanoparticles can have an average diameter of from 45 nm to 110 nm. The concentration of the nucleic acid active agents can be from 1 mg/mL to 10 mg/mL.

It was surprisingly found that lipid nanoparticles can survive lyophilization of the suspension, when the suspension is made into a protected composition.

In some embodiments, a protected composition of this invention can be composed of an aqueous suspension of the lipid nanoparticles in a pharmaceutically acceptable solution, a dextrin compound, and a saccharide sugar compound. The lipid nanoparticles can encapsulate an active agent, such as one or more nucleic acid active agents.

Lyophilization of the protected suspension can provide a solid lyophile product, which can be reconstituted into a suspension of lipid nanoparticles.

The reconstituted suspension can contain lipid nanoparticles, which encapsulate the active agent and are comparable to the lipid nanoparticles before lyophilization.

In certain embodiments, the reconstituted suspension can provide activity of the encapsulated agent, which is comparable to that of the suspension before lyophilization.

In further aspects, the reconstituted suspension can provide stable nanoparticles comparable to that of the suspension before lyophilization. In certain aspects, the average particle size of the nanoparticles can be nearly equal to the size of the nanoparticles in the suspension before lyophilization.

The compositions and processes of this invention can provide surprising activity and stability of a reconstituted suspension composed of nanoparticles having an encapsulated agent.

In further aspects, the protected suspension, which can be lyophilized and reconstituted, can contain a protectant composition for lyophilization. A protectant composition of this invention can be composed of a dextrin compound and a saccharide sugar compound. The total amount of the dextrin and sugar compounds may be from 2% to 20% (w/v) of the protected suspension.

In some embodiments, the dextrin compound can be from 40% to 70% (w/v) of the total amount of the dextrin and sugar compounds in the protectant composition. In certain embodiments, the dextrin compound can be from 40% to 55% (w/v) of the total amount of the dextrin and sugar compounds in the protectant composition. In further embodiments, the dextrin compound may be from 40% to 45% (w/v) of the total amount of the dextrin and sugar compounds in the protectant composition. These compositions can provide unexpectedly advantageous properties of a reconstituted nanoparticle suspension, for example, insignificant change of the nanoparticle size or activity.

In some aspects, upon lyophilization and reconstitution of a protected suspension of nanoparticles, the average size of the nanoparticles can be within 10% of their size in the original composition, before lyophilization. In certain aspects, upon lyophilization and reconstitution of a protected suspension of nanoparticles, the average size of the nanoparticles can be within 5% of their size in the original composition, before lyophilization.

This invention contemplates lipid nanoparticle drug formulations containing, for example, siRNA agents, which can be prepared by lyophilization of a suspension of the nanoparticles, and reconstitution of the nanoparticles into a suspension after a period of storage. The reconstituted suspension can provide activity of the encapsulated agent, which is comparable to that of the suspension before lyophilization.

The reconstituted suspension, prepared after a period of storage, can contain lipid nanoparticles, which encapsulate the active agent and are comparable to the lipid nanoparticles before lyophilization.

In certain embodiments, the reconstituted suspension, prepared after a period of storage, can provide activity of the encapsulated agent, which is comparable to that of the suspension before lyophilization.

In further aspects, the reconstituted suspension, prepared after a period of storage, can provide stable nanoparticles comparable to that of the suspension before lyophilization. In certain aspects, the average particle size of the nanoparticles can be nearly equal to the size of the nanoparticles in the suspension before lyophilization.

In some embodiments, the lyophilized composition can be stored at 5° C. for at least one month. In further embodiments, the lyophilized composition can be stored at −20° C. for at least one month.

Active Agents

The compositions and methods of this invention can be used to distribute agents for suppressing gene expression. Examples of an agent for suppressing gene expression include inhibitory nucleic acid molecules, including ribozymes, anti-sense nucleic acids, and RNA interference molecules (RNAi molecules).

Therapeutic compositions of this invention can include inhibitory nucleic acid molecules. Examples of nucleic acid molecules capable of mediating RNA interference include molecules active in RNA interference (RNAi molecules), including a duplex RNA such as an siRNA (small interfering RNA), miRNA (micro RNA), shRNA (short hairpin RNA), ddRNA (DNA-directed RNA), piRNA (Piwi-interacting RNA), or rasiRNA (repeat associated siRNA), and modified forms thereof.

Examples of active therapeutics of this invention include DNAs, plasmids, hybrid oligonucleotides, or aptamers.

The concentration of the active nucleic acid molecules in a pre-lyophilization formulation of this disclosure can be from about 1 mg/mL to about 10 mg/mL. In some embodiments, the concentration of the active nucleic acid molecules in a formulation of this disclosure can be from about 1 mg/mL to about 5 mg/mL, or from 2 mg/mL to 4 mg/mL.

Pre-Lyophilization Lipid Nanoparticle Formulations

Embodiments of this invention can provide compositions of lipid nanoparticles, which compositions contain a protectant compound for a lyophilization process.

The lipid nanoparticles can have any composition known in the art. The lipid nanoparticles may be synthesized and loaded with encapsulated cargo by any process, including processes known in the art.

In some embodiments, the lipid nanoparticles can be prepared by a submersion injection process. Some examples of processes for lipid nanoparticles are given in US 2013/0115274.

Some examples for preparing liposomes are given in Szoka, Ann. Rev. Biophys. Bioeng. 9:467 (1980); Liposomes, Marc J. Ostro, ed., Marcel Dekker, Inc., New York, 1983, Chapter 1.

In general, lipid nanoparticles can be synthesized by mixing lipid components in an organic solvent with an aqueous buffer solution containing active nucleic acid agents. The liposomes can be sized by filtration or extrusion. The liposome suspension or solution may be further transformed by diafiltration.

A lipid nanoparticle composition of this invention, which is stabilized for a lyophilization process, may contain lipid nanoparticles that encapsulate one or more active agents, such as nucleic acid agents, in a suspension. The suspension can be aqueous, and may contain a water-miscible solvent, such as ethanol. The composition, which is stabilized for a lyophilization process, may further contain protectant compounds to stabilize the liposomes in the lyophilization process.

The average size of lipid nanoparticles as synthesized can be from 40 nm to 120 nm, or from 45 nm to 110 nm, or from 85 nm to 105 nm.

The concentration of the active agent in a lipid nanoparticle composition of this invention can range from about 0.1 mg/mL to about 10 mg/mL. In some embodiments, the concentration of the active agent in a lipid nanoparticle composition of this invention can be from 0.5 mg/mL to 8 mg/mL, or from 1 mg/mL to 6 mg/mL, or from 2 mg/mL to 5 mg/mL, or from 3 mg/mL to 4 mg/mL.

Examples of protectant compounds include dextrin compounds.

Examples of dextrin compounds include maltodextrins, and beta- and gamma-cyclodextrins.

Examples of dextrin compounds include methylated beta- and gamma-cyclodextrin compounds, and sulfoalkyl ether beta- and gamma-cyclodextrin compounds.

Examples of dextrin compounds include cyclodextrin compounds having one or more of the 2, 3 and 6 hydroxyl positions substituted with sulfoalkyl, benzenesulfoalkyl, acetoalkyl, hydroxyalkyl, hydroxyalkyl succinate, hydroxyalkyl malonate, hydroxyalkyl glutarate, hydroxyalkyl adipate, hydroxyalkyl, hydroxyalkyl maleate, hydroxyalkyl oxalate, hydroxyalkyl fumarate, hydroxyalkyl citrate, hydroxyalkyl tartrate, hydroxyalkyl malate, or hydroxyalkyl citraconate groups.

Examples of dextrin compounds include (2-hydroxypropyl)-β-cyclodextrin, 2-hydroxypropyl-β-cyclodextrin succinate, (2-hydroxypropyl)-γ-cyclodextrin, and 2-hydroxypropyl-γ-cyclodextrin succinate.

Examples of dextrin compounds include hydroxyethyl β-cyclodextrin.

Examples of dextrin compounds include dimethyl β-cyclodextrin and trimethyl β-cyclodextrin.

Examples of dextrin compounds include sulfobutyl ether β-cyclodextrin and sulfobutyl ether γ-cyclodextrin.

Examples of dextrin compounds include methyl-β-cyclodextrin and methyl-γ-cyclodextrin.

Examples of dextrin compounds include hydroxypropyl-sulfobutyl-β-cyclodextrin.

Examples of dextrin compounds include H107 SIGMA cyclodextrin (Sigma-Aldrich Corp.).

Examples of dextrin compounds include CAVAMAX, CAVASOL, and CAVATRON cyclodextrins (Ashland Inc.).

Examples of dextrin compounds include KLEPTOSE and CRYSMEB cyclodextrins (Roquette America Inc.).

Examples of dextrin compounds include CAPTISOL cyclodextrins (Ligand Pharmaceuticals, Inc.).

In some embodiments, examples of dextrin compounds include dextrin compounds attached to a polymer chain or network. For example, cyclodextrin molecules can be attached to polymers of polyacrylic acid. In further embodiments, cyclodextrin molecules can be linked together with cross linking compounds such as acryloyl groups. In certain embodiments, vinyl acrylate hydrogel forms with attached cyclodextrin compounds can be used.

In some aspects, a dextrin compound to be used in a lipid nanoparticle composition of this invention can be combined with an adsorbate compound before being introduced into the lipid nanoparticle composition. Without wishing to be bound by any one particular theory, the pre-adsorption of a sterol compound by the dextrin compound may form an inclusion complex that can prevent a loss of activity of the active agent in the reconstituted drug product.

Examples of adsorbate compounds include cholesterol, lanosterol, zymosterol, zymostenol, desmosterol, stigmastanol, dihydrolanosterol, 7-dehydrocholesterol.

Examples of adsorbate compounds include pegylated cholesterols, and cholestane 3-oxo-(C1-22)acyl compounds, for example, cholesteryl acetate, cholesteryl arachidonate, cholesteryl butyrate, cholesteryl hexanoate, cholesteryl myristate, cholesteryl palmitate, cholesteryl behenate, cholesteryl stearate, cholesteryl caprylate, cholesteryl n-decanoate, cholesteryl dodecanoate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, and cholesteryl linoleate.

Examples of adsorbate compounds include phytosterols, beta-sitosterol, campesterol, ergosterol, brassicasterol, delta-7-stigmasterol, and delta-7-avenasterol.

Additional examples of protectant compounds include saccharide compounds. Examples of saccharide compounds include sugar compounds.

Examples of protectant sugar compounds include monosaccharides such as C(5-6) aldoses and ketoses, as well as disaccharides such as sucrose, lactose, lactulose, maltose, trehalose, cellobiose, kojibiose, sakebiose, isomaltose, sophorose, laminaribiose, gentiobiose, turanose, maltulose, isomaltulose, gentiobiulose, mannobiose, melibiose, melibiulose, and xylobiose.

Examples of protectant saccharide compounds include polysaccharides such as ficoll.

The concentration of protectant compounds in the pre-lyophilization formulation can be from about 1% (w/v) to about 25% (w/v).

In some embodiments, the concentration of protectant compounds in the pre-lyophilization formulation can be from 2% (w/v) to 20% (w/v), or from 4% (w/v) to 16% (w/v), or from 5% (w/v) to 15% (w/v), or from 6% (w/v) to 14% (w/v), or from 8% (w/v) to 12% (w/v).

In certain embodiments, the concentration of protectant compounds in the pre-lyophilization formulation can be 6% (w/v), or 8% (w/v), or 10% (w/v), or 12% (w/v), or 14% (w/v), or 16% (w/v), or 18% (w/v), or 20% (w/v), or 22% (w/v), or 24% (w/v).

Lyophilization Processes

Lyophilization processes can be carried out in any suitable vessel, such as glass vessels, or, for example, glass vials, or dual-chamber vessels, as are known in the pharmaceutical arts.

A stabilized lipid nanoparticle composition of this invention containing a protectant compound can be introduced into to the glass vessel. The volume of the composition added to the vessel can be from 0.1-20 mL, or from 1-10 mL.

Any lyophilization process can be used, including those known in the pharmaceutical arts. See, e.g., Remington's Pharmaceutical Sciences, 18th Ed., Mack Publishing Co., Easton, Penn. (1990).

The lyophilization process can include freezing the protectant-stabilized lipid nanoparticle composition at a temperature of from about −40° C. to about −30° C. The frozen composition can be dried form a lyophilized composition.

In some embodiments, the freezing step can ramp the temperature from ambient to the final temperature over several minutes. The temperature ramp can be about 1° C./minute.

In some embodiments, the drying step can be performed at a pressure of about 0-250 mTorr, or 50-150 mTorr, at a temperature of from about −15° C. to about −38° C. The drying step can be continued at a higher temperature, up to ambient temperature, over a period of up to several days. The level of residual water in the solid lyophile can be less than about 5%, or less than 4%, or less than 3%, or less than 2%, or less than 1% (w/v).

The protectant-stabilized lipid nanoparticle compositions of this invention, after lyophilization, can be reconstituted by methods known in the pharmaceutical arts.

In some aspects, this invention provides methods for inhibiting the level of aggregated particles in a reconstituted drug product, made from a protectant-stabilized lipid nanoparticle composition of this invention after lyophilization.

In some embodiments, the reconstituted drug product, made from a protectant-stabilized lipid nanoparticle composition of this invention after lyophilization, can have reduced levels of aggregate particles.

In certain embodiments, the reconstituted drug product, made from a protectant-stabilized lipid nanoparticle composition of this invention after lyophilization, can have reduced levels of aggregate particles with a size greater than about 0.2 µm, or greater than about 0.5 µm, or greater than about 1 µm.

Reconstituted Drug Product

The lyophile can be reconstituted in a pharmaceutically acceptable carrier.

Examples of a pharmaceutically acceptable carrier include sterile water, water for injection, sterile normal saline, bacteriostatic water for injection, and a nebulizer solution.

Examples of a pharmaceutically acceptable carrier include a pharmaceutically acceptable solution.

Examples of a pharmaceutically acceptable solution include HEPES buffer, phosphate buffers, citrate buffers, and a buffer containing Tris(hydroxymethyl)aminomethane.

Examples of a pharmaceutically acceptable solutions include pharmaceutically acceptable buffer solutions.

Examples of a pharmaceutically acceptable solution include buffer solutions of maleic acid, tartaric acid, lactic acid, acetic acid, sodium bicarbonate, and glycine.

The reconstituted lyophile can be used as a drug product.

The reconstituted lyophile can be further diluted with isotonic saline or other excipients to provide a predetermined concentration for administration.

Examples of excipients include tonicifiers.

Examples of excipients include stabilizers such as human serum albumin, bovine serum albumin, a-casein, globulins, a-lactalbumin, LDH, lysozyme, myoglobin, ovalbumin, and RNase A.

Examples of excipients include buffers such as potassium acetate, sodium acetate, and sodium bicarbonate.

Examples of excipients include amino acids such as glycine, alanines, arginine, betaine, leucine, lysine, glutamic acid, aspartic acid, histidine, proline, 4-hydroxyproline, sarcosine, γ-aminobutyric acid, alanopine, octopine, strombine, and trimethylamine N-oxide.

Examples of excipients include non-ionic surfactants such as polysorbate 20, polysorbate 80, and poloxamer 407.

Examples of excipients include dispersing agents such as phosphotidyl choline, ethanolamine, acethyltryptophanate, polyethylene glycol, polyvinylpyrrolidone, ethylene glycol, glycerin, glycerol, propylene glycol, sorbitol, xylitol, dextran, and gelatin.

Examples of excipients include antioxidants such as ascorbic acid, cysteine, thioglycerol, thioglycolic acid, thiosorbitol, and glutathione.

Examples of excipients include reducing agents such as dithiothreitol, thiols, and thiophenes.

Examples of excipients include chelating agents such as EDTA, EGTA, glutamic acid, and aspartic acid.

In some embodiments, the lyophile can be reconstituted using a syringe needle through a stoppered vial. The lyophile can be reconstituted with or without shaking the vial.

The time for reconstitution can be from 3-30 seconds, or longer.

In some embodiments, the reconstituted nucleic acid drug product can have less than 0.001% (w/v) of aggregate particles with a size greater than 0.2 µm.

In certain aspects, the reconstituted nucleic acid drug product can have reduced cytokine activation.

In additional aspects, the nucleic acid drug product can be reconstituted after a storage time period of six months and retain 80% activity of the nucleic acid agents.

In some embodiments, the nucleic acid drug product can be reconstituted after a storage time period of six months and the average particle size of the lipid nanoparticles can be less than 25% greater than before lyophilization.

In certain embodiments, the nucleic acid drug product can be reconstituted after a storage time period of 24 months and retain 90% activity of the nucleic acid agents.

In further embodiments, the nucleic acid drug product can be reconstituted after a storage time period of 24 months and the average particle size of the lipid nanoparticles can be less than 25% greater than before lyophilization.

RNAi Molecules

The amount of active RNA interference inducing ingredient formulated in the composition of the present invention may be an amount that does not cause an adverse effect exceeding the benefit of administration. Such an amount may be determined by an in vitro test using cultured cells, or a test in a model animal or mammal such as a mouse, a rat, a dog, or a pig, etc., and such test methods are known to those skilled in the art. The methods of this invention can be applicable to any animal, including humans.

The amount of active ingredient formulated can vary according to the manner in which the agent or composition is administered. For example, when a plurality of units of the composition is used for one administration, the amount of active ingredient to be formulated in one unit of the composition may be determined by dividing the amount of active ingredient necessary for one administration by said plurality of units.

The nucleic acid molecules and RNAi molecules of this invention can be delivered or administered to a cell, tissue, organ, or subject by direct application of the molecules in liposome formulations to assist, promote or facilitate entry into a cell.

The nucleic acid molecules and RNAi molecules of this invention can be complexed with cationic lipids, packaged within liposomes, and delivered to target cells or tissues. The nucleic acid or nucleic acid complexes can be locally administered to relevant tissues ex vivo, or in vivo through direct dermal application, transdermal application, or injection.

A inhibitory nucleic acid molecule or composition of this invention may be administered in unit dosage form. Conventional pharmaceutical practice may be employed to provide suitable formulations or compositions to administer the compounds to patients suffering from a disease. Any appropriate route of administration may be employed, for example, administration may be parenteral, intravenous, intraarterial, subcutaneous, intratumoral, intramuscular, intracranial, intraorbital, ophthalmic, intraventricular, intra-hepatic, intracapsular, intrathecal, intracisternal, intraperitoneal, intranasal, aerosol, suppository, or oral administration.

Compositions and methods of this disclosure can include an expression vector that includes a nucleic acid sequence encoding at least one RNAi molecule of this invention in a manner that allows expression of the nucleic acid molecule.

The nucleic acid molecules and RNAi molecules of this invention can be expressed from transcription units inserted into DNA or RNA vectors. Recombinant vectors can be DNA plasmids or viral vectors.

For example, the vector may contain sequences encoding both strands of a RNAi molecule of a duplex, or a single nucleic acid molecule that is self-complementary and thus forms a RNAi molecule. An expression vector may include a nucleic acid sequence encoding two or more nucleic acid molecules.

A nucleic acid molecule may be expressed within cells from eukaryotic promoters. Those skilled in the art realize that any nucleic acid can be expressed in eukaryotic cells from the appropriate DNA/RNA vector.

Lipid formulations can be administered to animals by intravenous, intramuscular, or intraperitoneal injection, or orally or by inhalation or other methods as are known in the art.

Pharmaceutically acceptable formulations for administering oligonucleotides are known and can be used.

In one embodiment of the above method, the inhibitory nucleic acid molecule is administered at a dosage of about 5 to 500 mg/m$^2$/day, e.g., 5, 25, 50, 100, 125, 150, 175, 200, 225, 250, 275, or 300 mg/m$^2$/day.

In some embodiments, the inhibitory nucleic acid molecules of this invention are administered systemically in dosages from about 1 to 100 mg/kg, e.g., 1, 5, 10, 20, 25, 50, 75, or 100 mg/kg.

In further embodiments, the dosage can range from about 25 to 500 mg/m$^2$/day.

Methods known in the art for making formulations are found, for example, in "Remington: The Science and Practice of Pharmacy" Ed. A. R. Gennaro, Lippincourt Williams & Wilkins, Philadelphia, Pa., 2000.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a neoplastic disease or condition. The preferred dosage of a nucleotide oligomer of the invention can depend on such variables as the type and extent of the disorder, the overall health status of the particular patient, the formulation of the compound excipients, and its route of administration.

Examples of Lipid Compositions

In certain embodiments, the four lipid-like components, i.e. one or more ionizable lipid molecules, a structural lipid, one or more stabilizer lipids, and one or more lipids for reducing immunogenicity of the composition, can be 100% of the lipid components of the composition.

Examples of lipid nanoparticle compositions are shown in Table 1.

TABLE 1

Compositions of lipid components (each in mol % of total)

| Ionizable | Cationic | Structural | Stabilizer | Reduce immun. |
|---|---|---|---|---|
| 17 | 0 | 35 | 40 | 8 |
| 20 | 0 | 35 | 40 | 5 |
| 25 | 0 | 35 | 39 | 1 |
| 25 | 0 | 35 | 35 | 5 |
| 25 | 0 | 30 | 40 | 5 |
| 25 | 0 | 40 | 30 | 5 |
| 30 | 0 | 25 | 40 | 5 |
| 35 | 0 | 25 | 35 | 5 |
| 40 | 0 | 30 | 25 | 5 |
| 25 | 5 | 30 | 35 | 5 |
| 25 | 10 | 30 | 30 | 5 |
| 25 | 15 | 25 | 30 | 5 |

Ionizable Lipid-Like Molecules

Examples of an ionizable molecule include compounds having the structure shown in Formula I

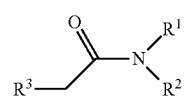

Formula I wherein $R^1$ and $R^2$ are $R^1 = CH_2(CH_2)_nOC(=O)R^4$ $R^2 = CH_2(CH_2)_mOC(=O)R^5$ wherein n and m are each independently from 1 to 2; and $R^4$ and $R^5$ are independently for each occurrence a C(12-20) alkyl group, or a C(12-20) alkenyl group; wherein $R^3$ is selected from 1-azetidines, 1-pyrrolidines, 1-piperidines, 4-morpholines, and 1,4-piperazines wherein the rings can be substituted at any carbon atom position,

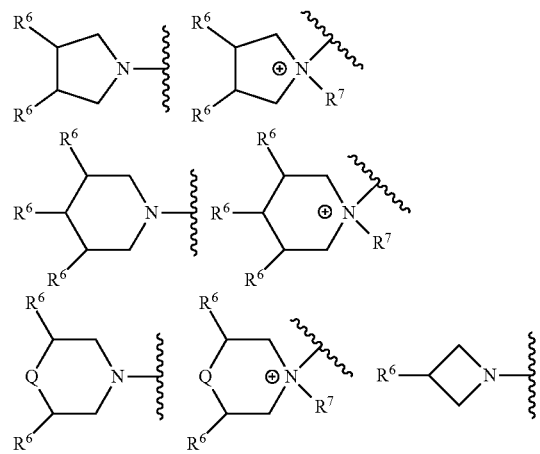

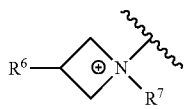

and can also be selected from amino and aminoalkyl groups, which may be substituted,

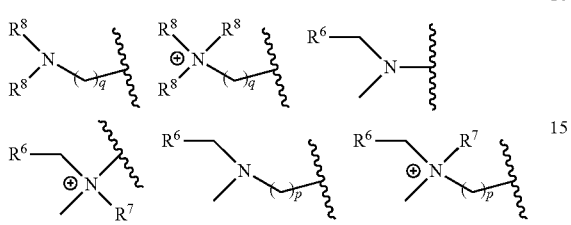

wherein
each $R^6$ is independently selected from H, alkyl, hydroxyl, hydroxyalkyl, alkoxy, alkoxyalkoxy, and aminoalkyl;
each $R^7$ is independently selected from H, alkyl, hydroxyalkyl, and aminoalkyl;
each $R^8$ is independently selected from H, alkyl, hydroxyalkyl, and aminoalkyl, and any two $R^8$ may form a ring;
q is from zero to four;
Q is O or $NR^7$;
p is from 1 to 4.

Examples of on ionizable lipid include the following compound:

COMPOUND A6

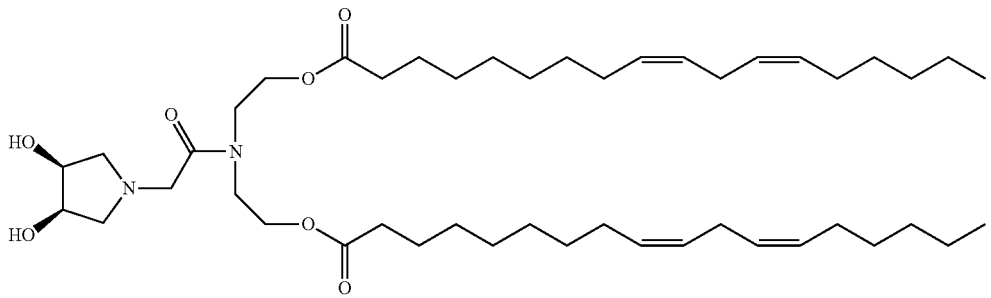

which is ((2-((3S,4R)-3,4-dihydroxypyrrolidin-1-yl)acetyl)azanediyl)bis(ethane-2,1-diyl) (9Z,9'Z,12Z,12'Z)-bis(octadeca-9,12-dienoate).

Examples of on ionizable lipid include the following compound:

COMPOUND A9

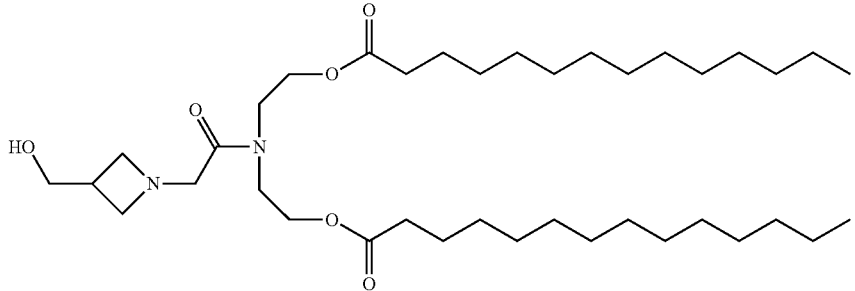

which is ((2-(3-(hydroxymethyl)azetidin-1-yl)acetyl) azanediyl)bis(ethane-2,1-diyl) ditetradecanoate.

Examples of on ionizable lipid include the following compound:

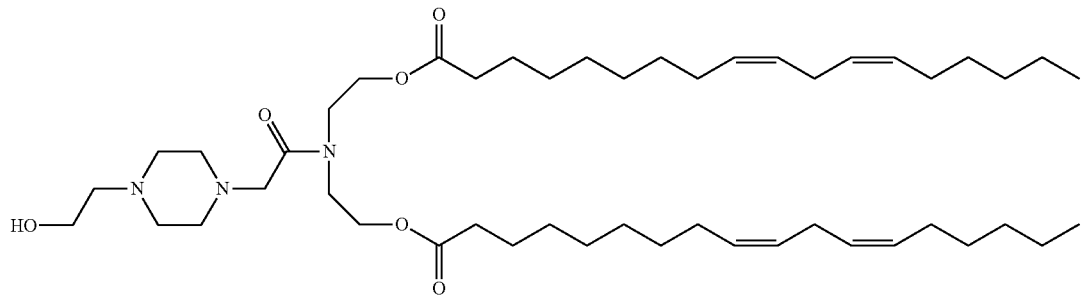

COMPOUND AA which is ((2-(4-(2-hydroxyethyl)piperazin-1-yl)acetyl) azanediyl)bis(ethane-2,1-diyl) (9Z,9'Z,12Z,12'Z)-bis(octadeca-9,12-dienoate).

Examples of on ionizable lipid include the following compound:

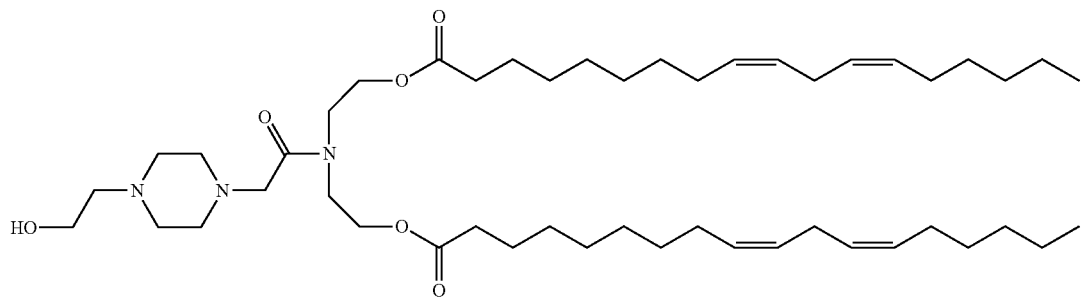

COMPOUND AB which is ((2-(4-(2-hydroxyethyl)piperazin-1-yl)acetyl) azanediyl)bis(ethane-2,1-diyl) (9Z,9'Z,12Z,12'Z)-bis(octadeca-9,12-dienoate).

Examples of on ionizable lipid include the following compound:

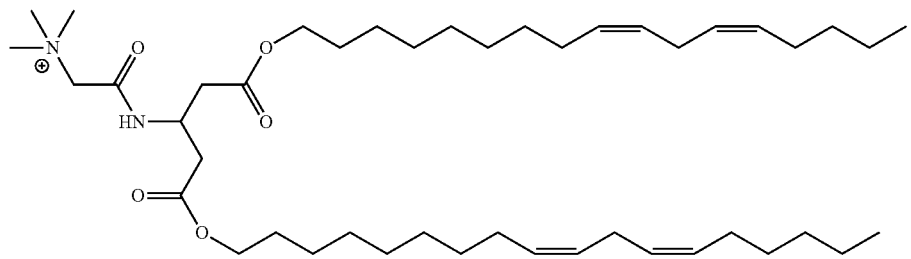

COMPOUND C2 which is 2-((1-(((9Z,12Z)-heptadeca-9,12-dien-1-yl)oxy)-5-(((9Z,12Z)-octadeca-9,12-dien-1-yl)oxy)-1,5-dioxopentan-3-yl)amino)-N,N,N-trimethyl-2-oxoethan-1-aminium.

Examples of on ionizable lipid include the following compound:

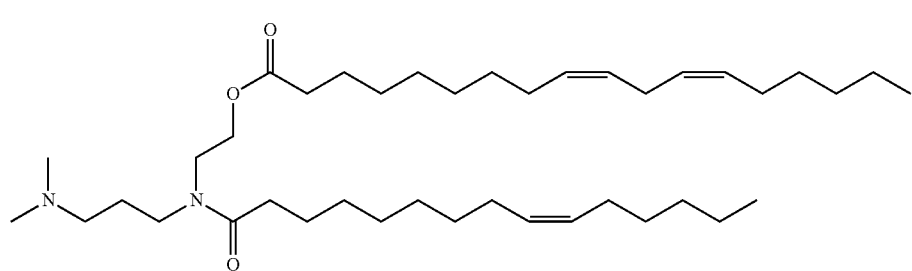

COMPOUND F5 which is 2-((9Z,12Z)—N-(3-(dimethylamino)propyl)octadeca-9,12-dienamido)ethyl (9Z,12Z)-octadeca-9,12-dienoate.

Examples of on ionizable lipid include the following compound:

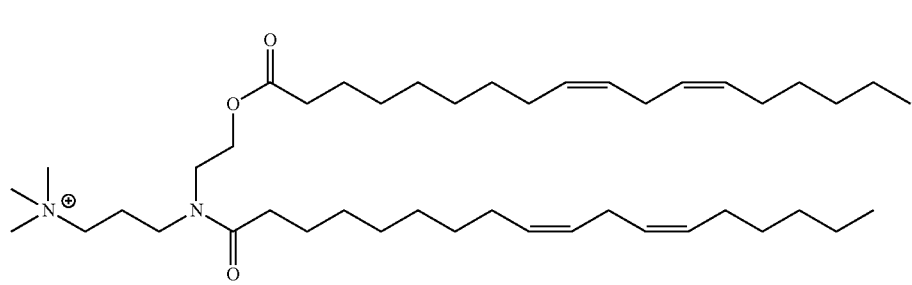

COMPOUND F7 which is N,N,N-trimethyl-3-((9Z,12Z)—N-(2-(((9Z,12Z)-octadeca-9,12-dienoyl)oxy)ethyl)octadeca-9,12-dienamido)propan-1-aminium.

Examples of on ionizable lipid include the following compound.

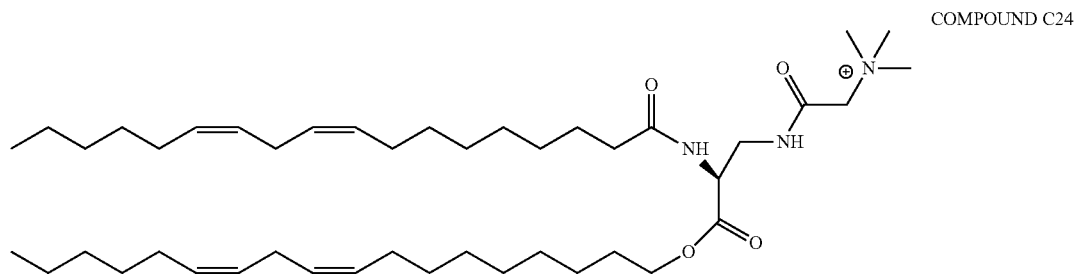 [SMILES: CCCCC/C=C\C/C=C\CCCCCCCCOC(=O)[C@H](CNC(=O)C[N+](C)(C)C)NC(=O)CCCCCCC/C=C\C/C=C\CCCCC]

COMPOUND C24 which is N,N,N-trimethyl-2-(((S)-3-(((9Z,12Z)-octadeca-9,12-dien-1-yl)oxy)-2-((9Z,12Z)-octadeca-9,12-dienamido)-3-oxopropyl)amino)-2-oxoethan-1-aminium.

Structural Lipids

Examples of structural lipids include cholesterols, sterols, and steroids.

Examples of structural lipids include cholanes, cholestanes, ergostanes, campestanes, poriferastanes, stigmastanes, gorgostanes, lanostanes, gonanes, estranes, androstanes, pregnanes, and cycloartanes.

Examples of structural lipids include sterols and zoosterols such as cholesterol, lanosterol, zymosterol, zymostenol, desmosterol, stigmastanol, dihydrolanosterol, and 7-dehydrocholesterol.

Examples of structural lipids include pegylated cholesterols, and cholestane 3-oxo-(C1-22)acyl compounds, for example, cholesteryl acetate, cholesteryl arachidonate, cholesteryl butyrate, cholesteryl hexanoate, cholesteryl myristate, cholesteryl palmitate, cholesteryl behenate, cholesteryl stearate, cholesteryl caprylate, cholesteryl n-decanoate, cholesteryl dodecanoate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, and cholesteryl linoleate.

Examples of structural lipids include sterols such as phytosterols, beta-sitosterol, campesterol, ergosterol, brassicasterol, delta-7-stigmasterol, and delta-7-avenasterol.

Stabilizer Lipids

Examples of stabilizer lipids include zwitterionic lipids.

Examples of stabilizer lipids include compounds such as phospholipids.

Examples of phospholipids include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine and ordilinoleoylphosphatidylcholine.

Examples of stabilizer lipids include phosphatidyl ethanolamine compounds and phosphatidyl choline compounds.

Examples of stabilizer lipids include 1,2-Dioleoyl-sn-Glycero-3-Phosphocholine (DOPC).

Examples of stabilizer lipids include diphytanoyl phosphatidyl ethanolamine (DPhPE) and 1,2-Diphytanoyl-sn-Glycero-3-Phosphocholine (DPhPC).

Examples of stabilizer lipids include 1,2-distearoyl-sn-glycero-3-phosphocholine (DSPC), 1,2-dipalmitoyl-sn-glycero-3-phosphocholine (DPPC), 1,2-dipalmitoyl-sn-glycero-3-phosphoethanolamine (DPPE), and 1,2-dioleoyl-sn-glycero-3-phosphoethanolamine (DOPE).

Examples of stabilizer lipids include 1,2-dilauroyl-sn-glycerol (DLG); 1,2-dimyristoyl-sn-glycerol (DMG); 1,2-dipalmitoyl-sn-glycerol (DPG); 1,2-distearoyl-sn-glycerol (DSG); 1,2-diarachidoyl-sn-glycero-3-phosphocholine (DAPC); 1,2-dilauroyl-sn-glycero-3-phosphocholine (DLPC); 1,2-dimyristoyl-sn-glycero-3-phosphocholine (DMPC); 1,2-dipalmitoyl-sn-glycero-O-ethyl-3-phosphocholine (DPePC); 1,2-dilauroyl-sn-glycero-3-phosphoethanolamine (DLPE); 1,2-dimyristoyl-sn-glycero-3-phosphoethanolamine (DMPE); 1,2-distearoyl-sn-glycero-3-phosphoethanolamine (DSPE); 1-palmitoyl-2-linoleoyl-sn-glycero-3-phosphocholine; 1-palmitoyl-2-oleoyl-sn-glycero-3-phosphocholine (POPC); 1-palmitoyl-2-lyso-sn-glycero-3-phosphocholine (P-Lyso-PC); and 1-Stearoyl-2-lyso-sn-glycero-3-phosphocholine (S-Lyso-PC).

Lipids for Reducing Immunogenicity

Examples of lipids for reducing immunogenicity include polymeric compounds and polymer-lipid conjugates.

Examples of lipids for reducing immunogenicity include pegylated lipids having polyethyleneglycol (PEG) regions. The PEG regions can be of any molecular mass. In some embodiments, a PEG region can have a molecular mass of 200, 300, 350, 400, 500, 550, 750, 1000, 1500, 2000, 3000, 3500, 4000 or 5000 Da.

Examples of lipids for reducing immunogenicity include compounds having a methoxypolyethyleneglycol region.

Examples of lipids for reducing immunogenicity include compounds having a carbonyl-methoxypolyethyleneglycol region.

Examples of lipids for reducing immunogenicity include compounds having a multi-branched PEG region.

Examples of lipids for reducing immunogenicity include compounds having a polyglycerine region.

Examples of lipids for reducing immunogenicity include polymeric lipids such as DSPE-mPEG, DMPE-mPEG, DPPE-mPEG, and DOPE-mPEG.

Examples of lipids for reducing immunogenicity include PEG-phospholipids and PEG-ceramides.

Cationic Lipids

Examples of cationic lipids include HEDC compounds described in US 2013/022665 A1, and other compounds described in US 2013/0330401 A1 and US 2013/0115274 A1. Additional examples of cationic lipids are known in the art.

Nanoparticle Formulations

Embodiments of this invention can provide liposome nanoparticle compositions.

In certain embodiments, an ionizable molecule of this invention can be used to form liposome compositions, which can have a bilayer of lipid-like molecules.

A nanoparticle composition can have one or more of the ionizable molecules of this invention in a liposomal structure, a bilayer structure, a micelle, a lamellar structure, or a mixture thereof.

In some embodiments, a composition can include one or more liquid vehicle components. A liquid vehicle suitable for delivery of active agents of this invention can be a pharmaceutically acceptable liquid vehicle. A liquid vehicle can include an organic solvent, or a combination of water and an organic solvent.

Embodiments of this invention can provide lipid nanoparticles having a size of from 10 to 1000 nm. In some embodiments, the liposome nanoparticles can have a size of from 10 to 150 nm.

In certain embodiments, the liposome nanoparticles of this invention can encapsulate the RNAi molecule and retain at least 80% of the encapsulated RNAi molecules after 1 hour exposure to human serum. This invention can provide a composition for use in distributing an active agent in cells, tissues or organs, organisms, and subjects, where the composition includes one or more ionizable lipid molecules of this invention.

Compositions of this invention may include one or more of the ionizable lipid molecules, along with a structural lipid, one or more stabilizer lipids, and one or more lipids for reducing immunogenicity of the composition.

An ionizable lipid molecule of this invention can be any mol % of a composition of this invention.

The ionizable lipid molecules of a composition of this invention can be from 15 mol % to 40 mol % of the lipid components of the composition. In certain embodiments, the ionizable lipid molecules of a composition can be from 20 mol % to 35 mol % of the lipid components of the composition. In further embodiments, the ionizable lipid molecules of a composition can be from 25 mol % to 30 mol % of the lipid components of the composition.

The structural lipid of a composition of this invention can be from 25 mol % to 40 mol % of the lipid components of the composition. In certain embodiments, the structural lipid of a composition can be from 30 mol % to 35 mol % of the lipid components of the composition.

The sum of the stabilizer lipids of a composition of this invention can be from 25 mol % to 40% mol % of the lipid components of the composition. In certain embodiments, the sum of the stabilizer lipids of a composition can be from 30 mol % to 40 mol % of the lipid components of the composition.

In some embodiments, a composition of this invention can include two or more stabilizer lipids, where each of the stabilizer lipids individually can be from 5 mol % to 35 mol % of the lipid components of the composition. In certain embodiments, a composition of this invention can include two or more stabilizer lipids, where each of the stabilizer lipids individually can be from 10 mol % to 30 mol % of the lipid components of the composition.

In certain embodiments, the sum of the one or more stabilizer lipids can be from 25 mol % to 40 mol % of the lipids of the composition, wherein each of the stabilizer lipids individually can be from 5 mol % to 35% mol %.

In certain embodiments, the sum of the one or more stabilizer lipids can be from 30 mol % to 40 mol % of the lipids of the composition, wherein each of the stabilizer lipids individually can be from 10 mol % to 30% mol %.

The one or more lipids for reducing immunogenicity of the composition can be from a total of 1 mol % to 8 mol % of the lipid components of the composition. In certain embodiments, the one or more lipids for reducing immunogenicity of the composition can be from a total of 1 mol % to 5 mol % of the lipid components of the composition.

In additional aspects, a composition of this invention can further include a cationic lipid, which can be from 5 mol % to 25 mol % of the lipid components of the composition. In certain embodiments, a composition of this invention can further include a cationic lipid, which can be from 5 mol % to 15 mol % of the lipid components of the composition. In these aspects, the molar ratio of the concentrations of the cationic lipid to the ionizable lipid molecules of a composition of this invention can be from 5:35 to 25:15.

In compositions of this invention, the entirety of the lipid components may include one or more of the ionizable lipid molecular components, one or more structural lipids, one or more stabilizer lipids, and one or more lipids for reducing immunogenicity of the composition.

In some embodiments, a composition can contain the ionizable lipid compound A6, the structural lipid cholesterol, the stabilizer lipids DOPC and DOPE, and the lipid for reducing immunogenicity DPPE-mPEG. In certain embodiments, compound A6 can be 15 to 25 mol % of the composition; the cholesterol, DOPC, and DOPE combined can be 75 to 85 mol % of the composition; and DPPE-mPEG can be 5 mol % of the composition.

In one embodiment, compound A6 can be 25 mol % of the composition; cholesterol can be 30 mol % of the composition, DOPC can be 20 mol % of the composition, DOPE can be 20 mol % of the composition; and DPPE-mPEG(2000) can be 5 mol % of the composition.

Pharmaceutical Compositions

This invention further contemplates methods for distributing an active agent to an organ of a subject for treating disease by administering to the subject a composition of this invention. Organs that can be treated include lung, liver, pancreas, kidney, colon, bone, skin, and intestine.

In further aspects, this invention provides a range of pharmaceutical formulations.

A pharmaceutical formulation herein can include an active agent, as well as a drug carrier, or a lipid of this invention, along with a pharmaceutically acceptable carrier or diluent. In general, active agents of this description include any active agents for malignant tumor, including any inhibitory nucleic acid molecules and any small molecular drugs. Examples of inhibitory nucleic acid molecules include ribozymes, anti-sense nucleic acids, and RNA interference molecules (RNAi molecules).

A pharmaceutical formulation of this invention may contain one or more of each of the following: a surface active agent, a diluent, an excipient, a preservative, a stabilizer, a dye, and a suspension agent.

Some pharmaceutical carriers, diluents and components for a pharmaceutical formulation, as well as methods for formulating and administering the compounds and compositions of this invention are described in Remington's Pharmaceutical Sciences, 18th Ed., Mack Publishing Co., Easton, Penn. (1990).

Examples of preservatives include sodium benzoate, ascorbic acid, and esters of p-hydroxybenzoic acid.

Examples of surface active agents include alcohols, esters, sulfated aliphatic alcohols.

Examples of excipients include sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, and calcium carboxymethyl cellulose.

Examples of suspension agents include coconut oil, olive oil, sesame oil, peanut oil, soya, cellulose acetate phthalate, methylacetate-methacrylate copolymer, and ester phthalates.

A therapeutic formulation of this invention for the delivery of one or more molecules active for gene silencing can be administered to a mammal in need thereof. A therapeutically effective amount of the formulation and active agent, which may be encapsulated in a liposome, can be administered to a mammal for preventing or treating malignant tumor.

The route of administration may be local or systemic.

A therapeutically-effective formulation of this invention can be administered by various routes, including intravenous, intraperitoneal, intramuscular, subcutaneous, and oral.

Routes of administration may include, for example, parenteral delivery, including intramuscular, subcutaneous, intravenous, intramedullary injections, as well as intrathecal, direct intraventricular, intraperitoneal, intranasal, or intraocular injections.

The formulation can also be administered in sustained or controlled release dosage forms, including depot injections, osmotic pumps, and the like, for prolonged and/or timed, pulsed administration at a predetermined rate.

The composition of the present invention may be administered via various routes including both oral and parenteral routes, and examples thereof include, but are not limited to, oral, intravenous, intramuscular, subcutaneous, local, intrapulmonary, intra-airway, intratracheal, intrabronchial, nasal, rectal, intraarterial, intraportal, intraventricular, intramedullar, intra-lymph-node, intralymphatic, intrabrain, intrathecal, intracerebroventricular, transmucosal, percutaneous, intranasal, intraperitoneal, and intrauterine routes, and it may be formulated into a dosage form suitable for each administration route. Such a dosage form and formulation method may be selected as appropriate from any known dosage forms and methods. See e.g. Hyojun Yakuzaigaku, Standard Pharmaceutics, Ed. by Yoshiteru Watanabe et al., Nankodo, 2003.

Examples of dosage forms suitable for oral administration include, but are not limited to, powder, granule, tablet, capsule, liquid, suspension, emulsion, gel, and syrup, and examples of the dosage form suitable for parenteral administration include injections such as an injectable solution, an injectable suspension, an injectable emulsion, and a ready-to-use injection. Formulations for parenteral administration may be a form such as an aqueous or nonaqueous isotonic sterile solution or suspension.

Pharmaceutical formulations for parenteral administration, e.g., by bolus injection or continuous infusion, include aqueous solutions of the active formulation in water-soluble form. Suspensions of the active compounds may be prepared as appropriate oily injection suspensions. Aqueous injection suspensions may contain substances, which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Formulations for injection may be presented in unit dosage form, e.g., in ampoules or in multi-dose containers, with an added preservative. The formulations may take such forms as suspensions, solutions or emulsions in oily or aqueous vehicles, and may contain formulary agents such as suspending, stabilizing and/or dispersing agents. Alternatively, the active ingredient may be in powder form for constitution with a suitable vehicle, e.g., sterile pyrogen-free water, before use.

In addition to the preparations described previously, the formulations may also be formulated as a depot preparation. Such long acting formulations may be administered by intramuscular injection. Thus, for example, the formulation may be formulated with suitable polymeric or hydrophobic materials, for example as an emulsion in an acceptable oil, or ion exchange resins, or as sparingly soluble derivatives, for example, as a sparingly soluble salt.

Compositions and formulations of this invention may also be formulated for topical delivery and may be applied to the subject's skin using any suitable process for application of topical delivery vehicle. For example, the formulation may be applied manually, using an applicator, or by a process that involves both. Following application, the formulation may be worked into the subject's skin, e.g., by rubbing. Application may be performed multiple times daily or on a once-daily basis. For example, the formulation may be applied to a subject's skin once a day, twice a day, or multiple times a day, or may be applied once every two days, once every three days, or about once every week, once every two weeks, or once every several weeks.

The formulations or pharmaceutical compositions described herein may be administered to the subject by any suitable means. Examples of methods of administration include, among others, (a) administration via injection, subcutaneously, intraperitoneally, intravenously, intramuscularly, intradermally, intraorbitally, intracapsularly, intraspinally, intrasternally, or the like, including infusion pump delivery; (b) administration locally such as by injection directly in the renal or cardiac area, e.g., by depot implantation; as well as deemed appropriate by those of skill in the art for bringing the active compound into contact with living tissue.

The exact formulation, route of administration and dosage for the pharmaceutical compositions can be chosen by the individual physician in view of the patient's condition. See, e.g., Goodman & Gilman's The Pharmacological Basis of Therapeutics, 12$^{th}$ Ed., Sec. 1, 2011. Typically, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some condition, the dosages will be about the same, or dosages that are about 0.1% to about 500%, more preferably about 25% to about 250% of the established human dosage. Where no human dosage is established, as will be the case for newly-discovered pharmaceutical compositions, a suitable human dosage can be inferred from ED50 or ID50 values, or other appropriate values derived from in vitro or in vivo studies, as qualified by toxicity studies and efficacy studies in animals.

EXAMPLES

Example 1: Preparation of siRNA Lipid Nanoparticle Drug Formulations by Lyophilization and Reconstitution Lipid nanoparticles were synthesized with high speed injection of lipid/ethanol solution into an siRNA buffer solution for about 10 minutes. Afterward, a second buffer, selected from citrate buffer pH 6.1, PBS pH 7.0, Tris pH 7.2, and HEPES pH 7.4, was diafiltered and used as the external buffer through TFF cartridges to make a final product aqueous suspension.

Various amounts of protectant compounds were added to the final product aqueous suspension, followed by 0.2/0.8 micrometer filtration. Lipid nanoparticles were prepared in either 500 mL or 1000 mL batches.

Results: It was surprisingly found that the lipid nanoparticles survived the lyophilization process, and that the lyophile provided a reconstituted suspension of lipid nanoparticles having an average particle size close to the size that was present in the original suspension.

Example 2: Reconstituted siRNA drug formulations of this invention exhibit stable particle size and siRNA encapsulation, which are suitable for use in drug products. The surprising level of stability of the siRNA formulations of this invention arises from the properties of the protected lyophilization composition.

In this study, a siRNA targeted to Hsp47 was formulated in liposomal nanoparticles with the following approximate composition: ionizable lipids, 40 mol %, DOPE, 30 mol %, Cholesterol, 25 mol %, and PEG-DMPE, 5.0 mol %.

The nanoparticle formulations were lyophilized with a protectant composition containing sucrose and (2-hydroxypropyl)-β-cyclodextrin. The total protectant content of the composition was 10% (w/v). The quantities used were 6% sucrose and 4% (2-hydroxypropyl)-β-cyclodextrin). Thus, the content of (2-hydroxypropyl)-β-cyclodextrin was 40% (w/v) of the total amount of sucrose plus (2-hydroxypropyl)-β-cyclodextrin.

Lipid nanoparticles were synthesized by high speed injection of lipid/ethanol solution into an siRNA buffer solution, to make a final product aqueous suspension. The initial bulk formulation of the siRNA-containing nanoparticles had an average nanoparticle size range of 99-101 nm.

The lyophilized, reconstituted siRNA drug formulations were tested for stability of particle size and encapsulation of the siRNA.

In general, it is most preferred that the siRNA nanoparticle formulations exhibit less than about 10% change in average particle size between the pre-lyophilized state and the lyophilized, reconstituted state. Further, it is most preferred that the siRNA nanoparticle formulations exhibit at least about 85% siRNA encapsulation efficiency of the lyophilized, reconstituted state.

The stability of the reconstituted siRNA nanoparticle products are shown in Table 2. In Table 2, the average particle size and siRNA encapsulation efficiency after lyophilization (AL) and reconstitution are shown along with similar results obtained from a frozen, thawed solution before lyophilization (BL).

TABLE 2

Nanoparticle stability before lyophilization and after reconstitution

| Total protectant | Z(avg) (nm) | | PDI | | Zeta (mV) | | % EE [siRNA] | | [siRNA] |
|---|---|---|---|---|---|---|---|---|---|
| % (w/v) | BL | AL | BL | AL | BL | AL | BL | AL | mg/ml |
| 10% (A)* | 105 | 108 | 0.140 | 0.167 | −1.4 | −1.7 | 91 | 86 | 1.9 |
| 10% (B) | 106 | 110 | 0.156 | 0.138 | −1.8 | −1.7 | 92 | 87 | 2.0 |
| 10% (C) | 106 | 108 | 0.150 | 0.165 | −2.0 | −1.7 | 92 | 87 | 1.9 |
| 10% (D) | 105 | 111 | 0.146 | 0.157 | −1.7 | −2.4 | 92 | 85 | 1.8 |
| 10% (A) | 106 | 111 | 0.134 | 0.149 | −1.5 | −1.1 | 93 | 88 | 3.7 |
| 12.5% (A) | 106 | 112 | 0.165 | 0.186 | −1.7 | −1.6 | 93 | 87 | 3.7 |
| 15% (A) | 105 | 112 | 0.170 | 0.141 | −1.3 | −1.1 | 93 | 87 | 3.6 |
| 15% (A) | 106 | 116 | 0.140 | 0.149 | −1.3 | −0.5 | 93 | 88 | 4.4 |
| 15% (B) | 105 | 116 | 0.154 | 0.157 | −1.3 | −0.7 | 93 | 88 | 4.4 |
| 15% (C) | 105 | 118 | 0.151 | 0.150 | −1.1 | −0.8 | 93 | 88 | 4.5 |

*In Table 2, (2-hydroxypropyl)-β-cyclodextrin) protectant compound from four different commercial sources A, B, C and D were used.

In Table 2, all protectant compositions exhibited suitable stability of the final reconstituted siRNA drug formulations. Except for samples at the highest levels of siRNA concentration and total protectant (15%), the siRNA nanoparticle formulations exhibited less than 10% change in average particle size between the pre-lyophilized state and the lyophilized, reconstituted state, as well as at least 85% siRNA encapsulation efficiency of the lyophilized, reconstituted state.

The results in Table 2 show that reconstituted siRNA drug formulations of this invention that were prepared from nanoparticle formulations by lyophilization from a protectant composition containing 60% sucrose and 40% (2-hydroxypropyl)-β-cyclodextrin were advantageously stable in average particle size and siRNA encapsulation efficiency.

Example 3: Dimethylnitrosamine (DMN) Induced Liver Fibrosis Rat Model

Reconstituted siRNA drug formulations of this invention exhibited profound and surprising potency for gene silencing in vivo. In vivo knockdown with lyophilized and reconstituted siRNA formulations was observed. siRNAs encapsulated in a liposomal formulation were used in a Dimethylnitrosamine (DMN) Induced Liver Fibrosis Rat Model.

A siRNA targeted to Hsp47 (GP46) was formulated in liposomal nanoparticles with the following approximate composition: ionizable lipids, 40 mol %, DOPE, 30 mol %, Cholesterol, 25 mol %, and PEG-DMPE, 5.0 mol %.

The nanoparticle formulations were lyophilized with a protectant composition containing sucrose and (2-hydroxypropyl)-β-cyclodextrin. The total protectant content was 10% (w/v). The content of (2-hydroxypropyl)-β-cyclodextrin was varied from 20% to 40% (w/v).

The samples were obtained as a fresh, same day lyophilized cake stored at −80 C. The samples were reconstituted with saline and further diluted with saline to a concentration of 0.17 mg/mL siRNA. Reconstitution time was about 20 s with 3 mL volume.

The final drug product reconstituted solutions of the Hsp47 siRNA were tested for in vivo potency, which is a rigorous test for the viability of lyophilized, reconstituted nanoparticles containing a nucleic acid agent.

Naïve Sprague Dawley rats in ten groups of 7-8 males with weight range 180-200 g were used in this study. A liquid dosage form with PBS at pH 7.4 was used. On the dosing day, prior to administration, formulation was reconstituted and diluted using saline into concentrations by group. The frozen control formulation was thawed and diluted one day before administration. An amount of DMN to achieve 5 mg/mL of clear dosing solution on the day of injection was added to PBS at pH 7.4. Administration was by intraperitoneal injection. Dosing was QD. Day 1-3, for 3 consecutive days. Dose was 0.5 to 1.5 mg/kg (siRNA) using formulation concentration range of 0.17-0.5 mg/mL, with administered volume 3 mL/kg. Rats were weighted before DMN administration and animals were injected on day 1-3 by intraperitoneal of 10 mg/kg of DMN (solution at 5 mg/ml), with dosing volume 2 mL/kg. On day 4-6, animals were injected with DMN with dosing volume 1 mL/kg. On day 5, DMN-treated animals were randomized into groups based on body weight (day 5) before the drug administration. Test article was administered on Day 6 (the first day of DMN injection was day 1). On day 7, rat livers were obtained and immediately flushed with PBS, pH 7.4 (40 mL at a rate of 20 mL/min) through clipped hepatic portal vein. One 2 mm thick transverse liver section was collected from the left lateral lobs.

gp46 mRNA knockdown evaluation. Total RNA from rat liver was extracted using RNeasy columns (Qiagen). RNA was quantified using a Nanodrop spectrophotometer.

As shown in FIG. 1, the reconstituted siRNA drug formulation of this invention that was protected with 40% (2-hydroxypropyl)-D-cyclodextrin exhibited profound and surprising potency for gene silencing of Hsp47 (GP46) in vivo.

In particular, the in vivo Hsp47 (GP46) gene silencing potency of the formulation protected with 40% (2-hydroxypropyl)-β-cyclodextrin was essentially 100%.

To the contrary, the in vivo potency of formulations containing 20% to 30% (2-hydroxypropyl)-β-cyclodextrin exhibited unacceptably low gene knockdown, being only 47% and 32%, respectively.

In sum, the unexpectedly advantageous result shows that protectant compositions for lyophilization of liposomal siRNA formulations of this invention can be made with at least 40% (2-hydroxypropyl)-β-cyclodextrin in a composition containing sucrose and (2-hydroxypropyl)-β-cyclodextrin.

Physical characterization showed that reconstituted siRNA drug formulations of this invention that were prepared from nanoparticle formulations by lyophilization from a protectant composition containing from about 40% to about 70% (2-hydroxypropyl)-β-cyclodextrin, and the remainder sucrose, were advantageously stable in average particle size. Below about 40% (2-hydroxypropyl)-β-cyclodextrin, the formulations tended to have anomalously increased encapsulation values, which is an indication of unwanted structural changes. Thus, the preferred range for the (2-hydroxypropyl)-β-cyclodextrin component was from about 40% to about 70%.

In conclusion, a reconstituted siRNA drug formulation of this invention utilizes from 40% to 70% (2-hydroxypropyl)-β-cyclodextrin with surprising potency for a nucleic acid drug agent in vivo.

Example 4: Reconstituted siRNA drug formulations of this invention exhibited sufficient plasma concentration for gene silencing in vivo. Plasma pharmacokinetics of lyophilized and reconstituted siRNA formulations was observed in vivo.

A siRNA targeted to Hsp47 (GP46) was formulated in liposomal nanoparticles with the following approximate composition: ionizable lipids, 40 mol %, DOPE, 30 mol %, Cholesterol, 25 mol %, and PEG-DMPE, 5.0 mol %.

The nanoparticle formulations were lyophilized with a protectant composition containing sucrose and (2-hydroxypropyl)-β-cyclodextrin. The total protectant content was 12.5% (w/v). The content of (2-hydroxypropyl)-β-cyclodextrin was 40% (w/v) of the total protectant, the remainder sucrose.

Plasma PK profiles were evaluated in Sprague Dawley rats following an intravenous administration at a single dose level of the lyophilized formulation compared to a frozen formulation. siRNA concentrations in plasma samples were determined by a hybridization-based ELISA method. Sprague-Dawley rats were prepared with a double jugular vein catheter. Animals were given a single bolus intravenous dose injection of the test material via one jugular vein catheter over 15 seconds at Day 1. Approximately 0.30 mL of whole blood was collected from the jugular vein catheter of each animal into K2EDTA tubes at each time point.

Figure 2:
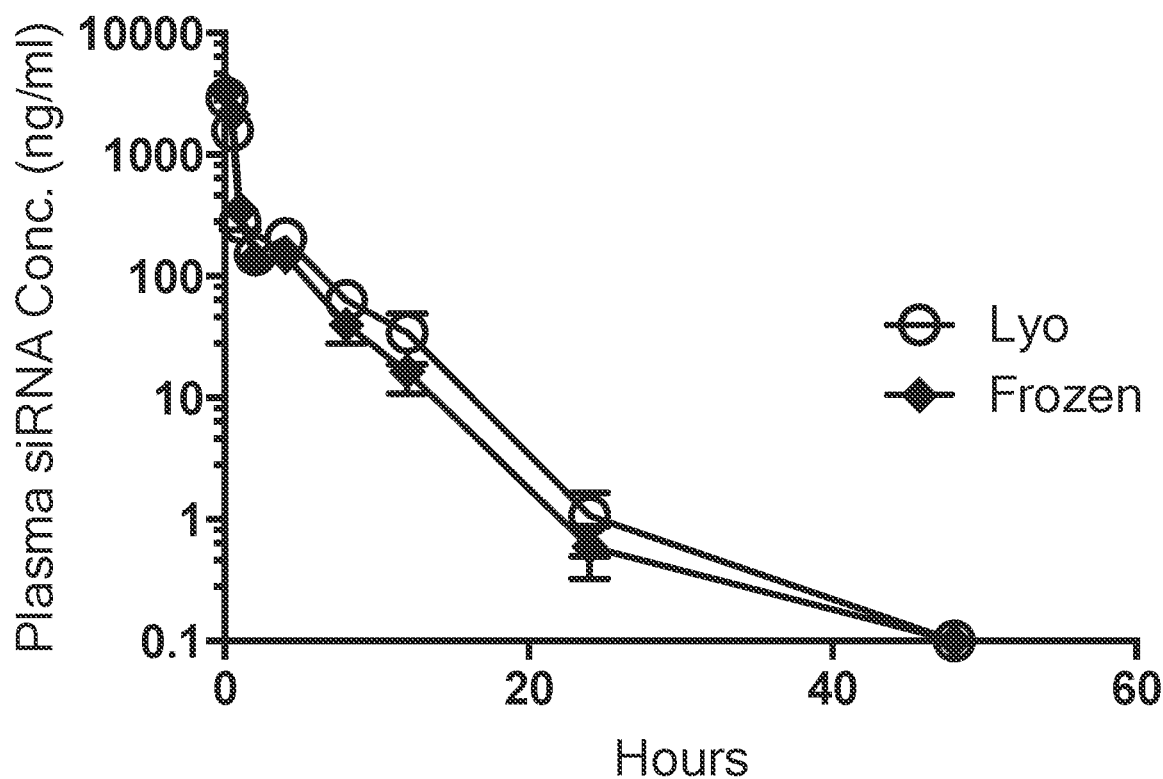
FIG. 2 shows experimental results for plasma concentration pharmacokinetics in vivo of a lyophilized, reconstituted siRNA nanoparticle formulation. A siRNA targeted to Hsp47 (GP46) was formulated in liposomal nanoparticles. The nanoparticle formulations were lyophilized with a protectant composition containing sucrose and (2-hydroxypropyl)-β-cyclodextrin. The nanoparticle formulation of the siRNA that was lyophilized included a total protectant content of 12.5% (w/v), which was composed of 40% (w/v) (2-hydroxypropyl)-β-cyclodextrin and 60% sucrose. Plasma PK profiles were evaluated in Sprague Dawley rats following an intravenous administration at a single dose level of the lyophilized formulation compared to a frozen formulation. siRNA concentrations in plasma samples were determined by a hybridization-based ELISA method.

As shown in FIG. 2, the plasma concentration pharmacokinetics of the lyophilized, reconstituted siRNA drug formulation was essentially the same as a comparative control formulation that had only been frozen. The lyophilized, reconstituted siRNA nucleic acid drug formulation provided surprisingly efficient levels of drug agent in plasma.

For this experiment, the area under the time-concentration curve (AUC) and the peak plasma concentration (Cmax) after a single dose are shown in Table 3.

TABLE 3

Plasma pharmacokinetics for lyophilized, reconstituted nucleic acid formulations

|  | Reconstituted | Frozen |
| --- | --- | --- |
| AUC | 2751 | 2683 |
| Cmax | 2922 | 3350 |

In conclusion, this experiment shows that the plasma concentration pharmacokinetics of a lyophilized, reconstituted nucleic acid drug formulation was essentially the same as a comparative positive control formulation that had only been frozen. Thus, the lyophilized, reconstituted siRNA nucleic acid drug formulation provided surprisingly efficient levels of drug agent in plasma, and was not degraded relative to a non-lyophilized composition.

Example 5: Protecting Lipid Nanoparticles in the 100 nm Size Range

Lipid nanoparticles were synthesized with dispersion of lipid/ethanol solution into a siRNA buffer, to make a final product aqueous suspension. The nanoparticles had an average size of 105-106 nm. The nanoparticles were synthesized using compound HEDC as an ionizable lipid (see, e.g. US 2013/022665 A1). The nanoparticles encapsulated a siRNA targeted to Hsp47.

Table 4 shows the nanoparticle characteristics before lyophilization, where the final product aqueous suspension was merely frozen, then thawed. Table 5 shows the nanoparticle characteristics after lyophilization.

The increase in average particle size from Table 4 to Table 5 is only 6.7%.

TABLE 4

Nanoparticle characteristics before lyophilization (100 nm size range)

| | Sucrose/ | Pre-lyophilization (Frozen) | | | | |
| --- | --- | --- | --- | --- | --- | --- |
| No. | 2HPBCD (wt %/wt %) | Z(avg) (nm) | PDI | Zeta (mV) | EE (%) | [siRNA] (mg/ml) | yield (%) |
| 1 | 6/4 | 105 | 0.14 | −1.4 | 91 | 2.1 | 103 |
| 2 | 6/4 | 106 | 0.16 | −1.8 | 92 | 2.1 | 105 |
| 3 | 6/4 | 106 | 0.15 | −2.0 | 92 | 2.1 | 104 |
| 4 | 6/4 | 105 | 0.15 | −1.7 | 92 | 2.1 | 104 |
| 5 | 6/4 | 106 | 0.14 | −1.3 | 93 | 5.1 | 101 |
| 6 | 6/4 | 105 | 0.15 | −1.3 | 93 | 4.9 | 99 |
| 7 | 6/4 | 105 | 0.15 | −1.1 | 93 | 5.2 | 103 |
| 8 | 6/4 | 106 | 0.16 | −0.9 | 93 | 5.2 | 104 |

TABLE 5

Nanoparticle characteristics after lyophilization (100 nm size range)

| | Sucrose/ | Post-lyophilization (Reconstituted) | | | | |
| --- | --- | --- | --- | --- | --- | --- |
| No. | 2HPBCD (wt %/wt %) | Z(avg) (nm) | PDI | Zeta (mV) | EE (%) | [siRNA] (mg/ml) | yield (%) |
| 1 | 6/4 | 108 | 0.17 | −1.7 | 86 | 1.9 | 94 |
| 2 | 6/4 | 110 | 0.14 | −1.7 | 87 | 2.0 | 98 |
| 3 | 6/4 | 108 | 0.16 | −1.7 | 87 | 1.9 | 95 |
| 4 | 6/4 | 111 | 0.16 | −2.4 | 85 | 1.8 | 92 |
| 5 | 6/4 | 116 | 0.15 | −0.5 | 88 | 4.4 | 88 |
| 6 | 6/4 | 116 | 0.16 | −0.7 | 88 | 4.4 | 89 |
| 7 | 6/4 | 118 | 0.15 | −0.8 | 88 | 4.5 | 90 |
| 8 | 6/4 | 114 | 0.12 | −1.3 | 87 | 4.42 | 88 |

In an additional test, nine final product solutions containing 6% (w/v) sucrose, 4% (w/v) (2-hydroxypropyl)-β-cyclodextrin, and a concentration of a siRNA targeted to Hsp47 of 2 mg/mL were tested for average particle size increase upon lyophilization and reconstitution. After lyophilization, the reconstituted drug products showed surprisingly little increase in average particle size of less than 5%, from 102 nm to 107 nm, as compared to the final product solutions before lyophilization.

Example 6: Protecting Lipid Nanoparticles in the 50 nm Size Range

Lipid nanoparticles were synthesized with high speed injection of lipid/ethanol solution into an siRNA buffer, to make a final product aqueous suspension. The nanoparticles had an average size of 48-50 nm. The nanoparticles were synthesized using Compound A6 as an ionizable lipid. The nanoparticles encapsulated a siRNA targeted to Hsp47 at 2 mg/mL.

Table 6 shows the nanoparticle characteristics before lyophilization (BL) and after lyophilization (AL) of nanoparticles in the 50 nm range.

TABLE 6

Nanoparticle characteristics before and after lyophilization of nanoparticles in the 50 nm range

| Sucrose/2HPBCD | Z(avg) (nm) | | PDI | | Zeta (mV) | | % EE | |
|---|---|---|---|---|---|---|---|---|
| (wt %/wt %) | BL | AL | BL | AL | BL | AL | BL | AL |
| 5/5 | 48 | 53 | 0.07 | 0.13 | −2.3 | −3.3 | 76 | 66 |
| 6/4 | 48 | 51 | 0.07 | 0.14 | −2.8 | −4.8 | 81 | 68 |
| 12/0 | 50 | 75 | 0.08 | 0.25 | −4.9 | −2.0 | 86 | 81 |

Example 7: Protecting siRNA Lipid Nanoparticles for Long Term Storage

Reconstituted siRNA drug formulations of this invention exhibited long term stability for gene silencing in vivo.

A siRNA targeted to Hsp47 (GP46) was formulated in liposomal nanoparticles with the following approximate composition: ionizable lipids, 40 mol %, DOPE, 30 mol %, Cholesterol, 25 mol %, and PEG-DMPE, 5.0 mol %.

The nanoparticle formulations were lyophilized with a protectant composition containing sucrose and (2-hydroxypropyl)-β-cyclodextrin. The total protectant content was from 10% to 12.5% to 15% (w/v). The content of (2-hydroxypropyl)-β-cyclodextrin was 40% (w/v), sucrose 60%. The cyclodextrin was CAVITRON W7 HP5 PHARMA cyclodextrin.

The vials were stored at temperatures shown in Table 7 for 4 weeks. After storage and reconstitution, the average size of the nanoparticles (PS, Z-avg) was surprisingly stable, as shown in Table 7.

As shown in Table 7, the size of the siRNA nanoparticles was within 4% of their size in the original composition.

TABLE 7

Nanoparticle characteristics

| Sample | Temperature −20 C. | | | | Temperature 5 C. | | | |
|---|---|---|---|---|---|---|---|---|
| total % | Initial Z-avg | | 1 mo Z-avg | | Initial Z-avg | | 1 mo Z-avg | |
| protectant | Z-avg | PDI | Z-avg | PDI | Z-avg | PDI | Z-avg | PDI |
| 10 | 103 | 0.12 | 99 | 0.15 | 103 | 0.12 | 102 | 0.14 |
| 12.5 | 101 | 0.13 | 101 | 0.15 | 101 | 0.13 | 100 | 0.16 |
| 15 | 102 | 0.13 | — | — | 102 | 0.13 | 102 | 0.15 |
| 10 | 100 | 0.13 | 99 | 0.17 | 100 | 0.13 | 96 | 0.16 |
| 12.5 | 95 | 0.16 | 94 | 0.14 | 95 | 0.16 | 94 | 0.14 |
| 15 | 96 | 0.13 | 95 | 0.13 | 96 | 0.13 | 96 | 0.13 |
| 10 | 95 | 0.15 | 95 | 0.16 | 95 | 0.15 | 96 | 0.15 |
| 12.5 | 95 | 0.15 | 92 | 0.11 | 95 | 0.15 | 93 | 0.14 |
| 15 | 94 | 0.13 | 92 | 0.14 | 94 | 0.13 | 91 | 0.14 |

Example 8: Protecting siRNA Lipid Nanoparticles for Long Term Storage

Reconstituted siRNA drug formulations of this invention exhibited long term stability for gene silencing in vivo.

A siRNA targeted to Hsp47 (GP46) was formulated in liposomal nanoparticles with the following approximate composition: ionizable lipids, 40 mol %, DOPE, 30 mol %, Cholesterol, 25 mol %, and PEG-DMPE, 5.0 mol %.

The nanoparticle formulations were lyophilized with a protectant composition containing sucrose and (2-hydroxypropyl)-β-cyclodextrin. The total protectant content was from 10% to 12.5% to 15% (w/v). The content of (2-hydroxypropyl)-β-cyclodextrin was 40% (w/v), sucrose 60%. The cyclodextrin was CAVITRON W7 HP7 PHARMA cyclodextrin.

The vials were stored at temperatures shown in Table 8 for 4 weeks. After storage and reconstitution, the average size of the nanoparticles (PS, Z-avg) was surprisingly stable, as shown in Table 8.

As shown in Table 8, the size of the siRNA nanoparticles was within 5% of their size in the original composition.

TABLE 8

Nanoparticle characteristics

| Sample | Temperature −20 C. | | | | Temperature 5 C. | | | |
|---|---|---|---|---|---|---|---|---|
| total % | Initial Z-avg | | 1 mo Z-avg | | Initial Z-avg | | 1 mo Z-avg | |
| protectant | Z-avg | PDI | Z-avg | PDI | Z-avg | PDI | Z-avg | PDI |
| 10 | 103 | 0.11 | 99 | 0.14 | 103 | 0.11 | 99 | 0.15 |
| 12.5 | 101 | 0.14 | 99 | 0.15 | 101 | 0.14 | 98 | 0.15 |
| 15 | 102 | 0.15 | — | — | 102 | 0.15 | 97 | 0.14 |
| 10 | 96 | 0.13 | 95 | 0.13 | 96 | 0.13 | 93 | 0.13 |
| 12.5 | 94 | 0.12 | 91 | 0.12 | 94 | 0.12 | 91 | 0.13 |
| 15 | 94 | 0.13 | 89 | 0.14 | 94 | 0.13 | 91 | 0.14 |
| 10 | 94 | 0.15 | 89 | 0.15 | 94 | 0.15 | 89 | 0.13 |
| 12.5 | 91 | 0.15 | 87 | 0.13 | 91 | 0.15 | 88 | 0.14 |
| 15 | 90 | 0.14 | 86 | 0.15 | 90 | 0.14 | 87 | 0.12 |

All publications, patents and literature specifically mentioned herein are incorporated by reference in their entirety for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention. It will be readily apparent to one skilled in the art that varying substitutions and modifications can be made to the description disclosed herein without departing from the scope and spirit of the description, and that those embodiments are within the scope of this description and the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably, and shall be read expansively and without limitation.

Recitation of ranges of values herein are merely intended to serve as a shorthand method of referring individually to each separate value falling within the range, unless otherwise indicated herein, and each separate value is incorporated into the specification as if it were individually recited herein. For Markush groups, those skilled in the art will recognize that this description includes the individual members, as well as subgroups of the members of the Markush group.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A process for making a nucleic acid drug product, the process comprising:
   synthesizing lipid nanoparticles, wherein the lipid nanoparticles encapsulate one or more nucleic acid active agents;
   providing an aqueous suspension of the lipid nanoparticles in a pharmaceutically acceptable solution;
   adding a dextrin compound to the solution containing the lipid nanoparticles;
   adding a saccharide sugar compound to the solution containing the lipid nanoparticles;
   lyophilizing the solution containing the lipid nanoparticles, thereby forming a solid lyophile; and
   reconstituting the lyophile in a pharmaceutically acceptable carrier, thereby forming a nucleic acid drug product,
   wherein the total amount of the dextrin and saccharide sugar compounds is from 10% to 12% (w/v) of the solution containing the lipid nanoparticles, and
   wherein the dextrin compound is from 40% to 45% (w/v) of the total amount of the dextrin and saccharide sugar compounds,
   wherein the lipid nanoparticles comprise a compound selected from the group consisting of compound A6, compound A9, compound AA, compound AB, compound C2, compound F5, compound F7, compound C24, and hydroxyethyl disulfide cholesterol (HEDC),
   wherein the compound A6 is:

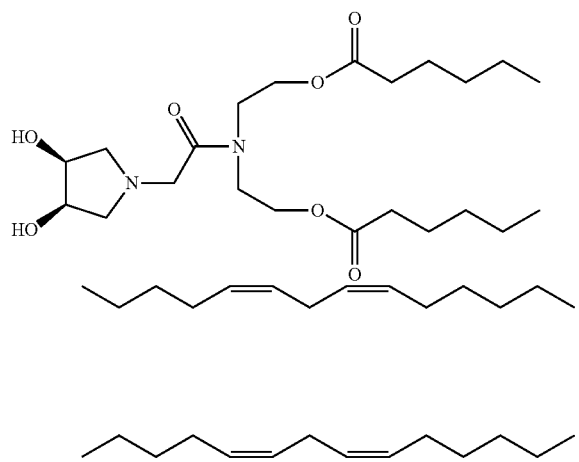

the compound A9 is:

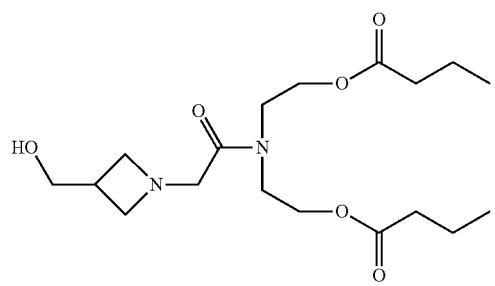

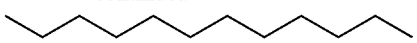

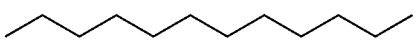

the compound AA is:

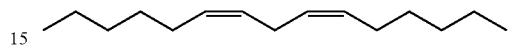

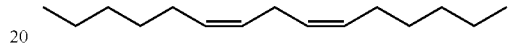

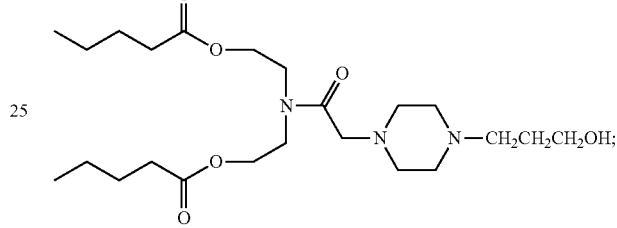

the compound AB is:

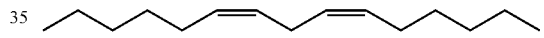

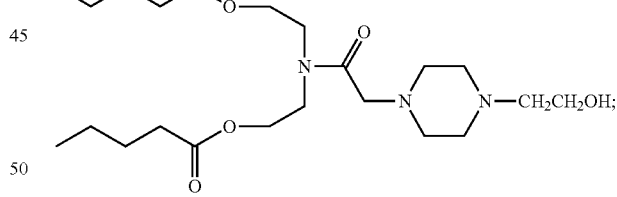

the compound C2 is:

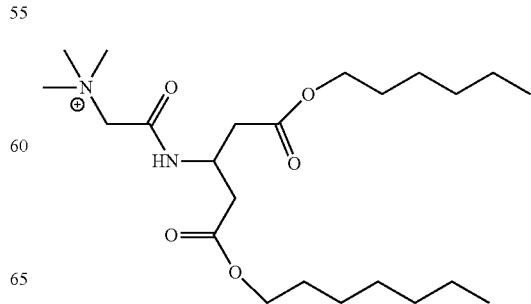

-continued

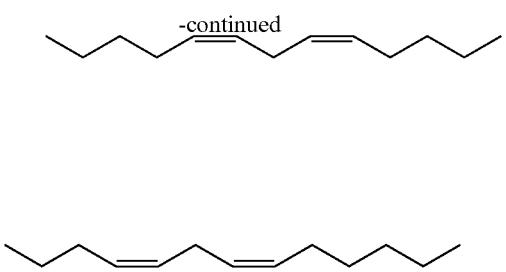

;

the compound F5 is:

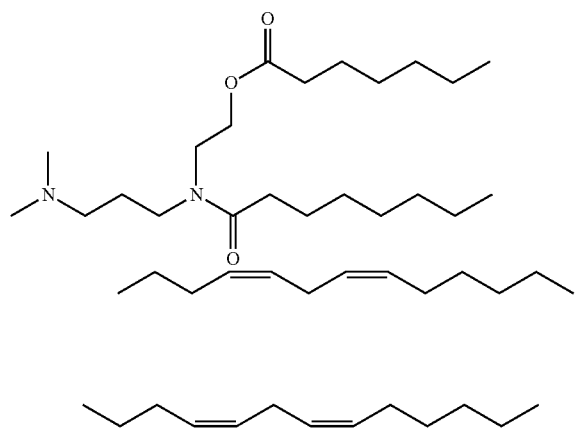

;

the compound F7 is:

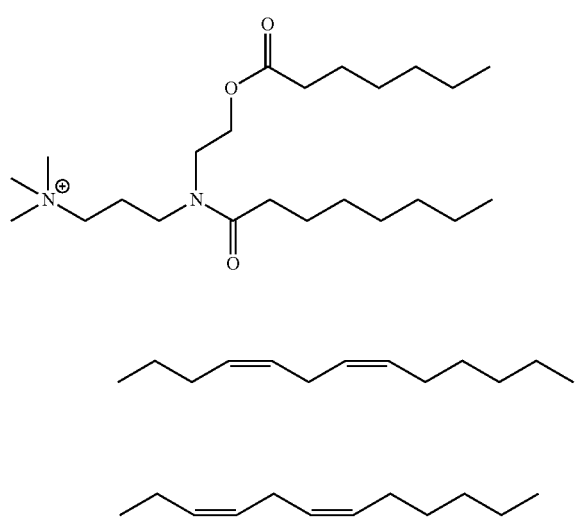

and
the compound C24 is:

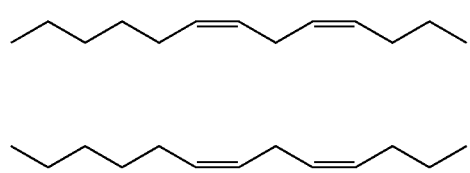

-continued

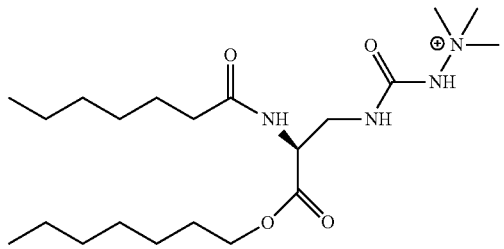

;

2. The process of claim 1, wherein upon reconstitution, the change of average size of the nanoparticles is within 10% of their size when synthesized.

3. The process of claim 1, further comprising storing the lyophile before reconstitution,
wherein upon storage and reconstitution of the lyophile, the change of average size of the nanoparticles is within 10% of their size when synthesized, and
wherein the lyophile is stored at 5 or −20° C. for at least one month.

4. The process of claim 1, wherein the nanoparticles have an average diameter of from 45 nm to 110 nm.

5. The process of claim 1, wherein the concentration of the nucleic acid active agents is from 1 mg/mL to 10 mg/mL.

6. The process of claim 1, wherein the one or more nucleic acid active agents are RNAi molecules capable of mediating RNA interference.

7. The process of claim 1, wherein the pharmaceutically acceptable solution is a HEPES buffer, a phosphate buffer, a citrate buffer, or a buffer containing Tris(hydroxymethyl) aminomethane.

8. The process of claim 1, wherein the dextrin compound is a cyclodextrin.

9. The process of claim 8, wherein the cyclodextrin compound has one or more of the 2, 3 and 6 hydroxyl positions substituted with sulfoalkyl, benzenesulfoalkyl, acetoalkyl, hydroxyalkyl, hydroxyalkyl succinate, hydroxyalkyl malonate, hydroxyalkyl glutarate, hydroxyalkyl adipate, hydroxyalkyl, hydroxyalkyl maleate, hydroxyalkyl oxalate, hydroxyalkyl fumarate, hydroxyalkyl citrate, hydroxyalkyl tartrate, hydroxyalkyl malate, or hydroxyalkyl citraconate groups.

10. The process of claim 8, wherein the cyclodextrin compound is (2-hydroxypropyl)-β-cyclodextrin, 2-hydroxypropyl-β-cyclodextrin succinate, (2-hydroxypropyl)-γ-cyclodextrin, or 2-hydroxypropyl-γ-cyclodextrin succinate.

11. The process of claim 8, wherein the cyclodextrin compound is sulfobutyl ether β-cyclodextrin or sulfobutyl ether γ-cyclodextrin.

12. The process of claim 8, wherein the cyclodextrin compound is methyl-β-cyclodextrin or methyl-γ-cyclodextrin.

13. The process of claim 8, wherein the cyclodextrin compound includes an adsorbate compound.

14. The process of claim 1, wherein the saccharide sugar compound is a monosaccharide or disaccharide sugar compound.

15. The process of claim 1, wherein the pharmaceutically acceptable carrier is sterile water, water for injection, sterile normal saline, bacteriostatic water for injection, or a nebulizer solution.

16. The process of claim 1, wherein the pharmaceutically acceptable carrier is a pharmaceutically acceptable solution.

17. The process of claim 1, wherein the reconstituted nucleic acid drug product has less 0.001% (w/v) of aggregate particles with a size greater than 0.2 μm.

18. The process of claim 1, wherein the nucleic acid drug product is reconstituted in a time period of 3 to 30 seconds.

19. The process of claim 1, wherein the nucleic acid drug product is reconstituted after a storage time period of six months and retains 80% activity of the nucleic acid agents.

* * * * *

UNITED STATES PATENT AND TRADEMARK OFFICE
CERTIFICATE OF CORRECTION

| | | |
|---|---|---|
| PATENT NO. | : 12,311,055 B2 | |
| APPLICATION NO. | : 18/346115 | |
| DATED | : May 27, 2025 | |
| INVENTOR(S) | : Adami et al. | |

It is certified that error appears in the above-identified patent and that said Letters Patent is hereby corrected as shown below:

On the Title Page

Column 1 (Related U.S. Application Data), Line 1, delete "(60)" and insert -- (63) --.

In the Specification

Column 3, Line 60, delete "isomaltulose, gentiobiulose, mamiobiose," and insert -- isomaltulose, gentiobiose, mamiobiose, --.

Column 10, Line 28, delete "isomaltulose, gentiobiulose, mamiobiose," and insert -- isomaltulose, gentiobiose, mamiobiose, --.

Column 11, Line 61, delete "phosphotidyl choline," and insert -- phosphatidyl choline, --.

Column 11, Line 61, delete "ethanolamine, acethyltryptophanate," and insert -- ethanolamine, acetyltryptophanate, --.

Column 13, Line 41, delete "Gennaro, Lippincourt Williams" and insert -- Gennaro, Lippincott Williams --.

Column 13, Line 46, delete "hydrogenated napthalenes. Biocompatible" and insert -- hydrogenated naphthalenes. Biocompatible --.

Signed and Sealed this
Thirtieth Day of September, 2025

John A. Squires
*Director of the United States Patent and Trademark Office*

CERTIFICATE OF CORRECTION (continued)
U.S. Pat. No. 12,311,055 B2

Page 2 of 2

Under Column 19-20, Line 2-7 (approx.), delete "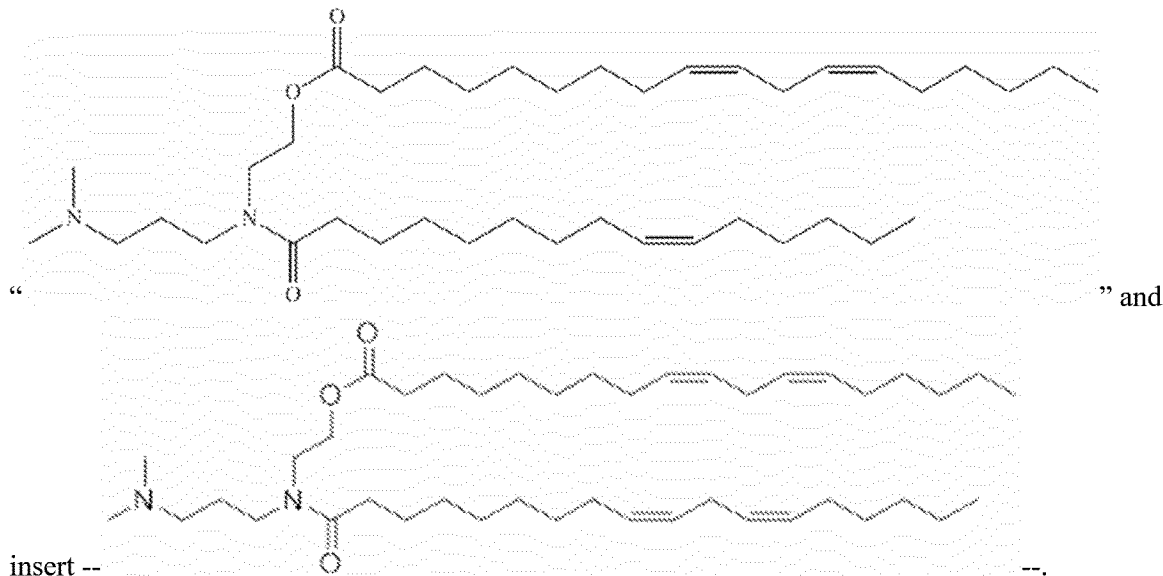" and insert -- --.

Column 24, Line 62-63, delete "intraventricular, intramedullar, intra" and insert -- intraventricular, intramedullary, intra --.

Column 28, Line 43, delete "hydroxypropyl)-D-cyclodextrin" and insert -- hydroxypropyl)-β-cyclodextrin --.

In the Claims

Column 36, Claim 1, Line 2-12 (approx.), delete "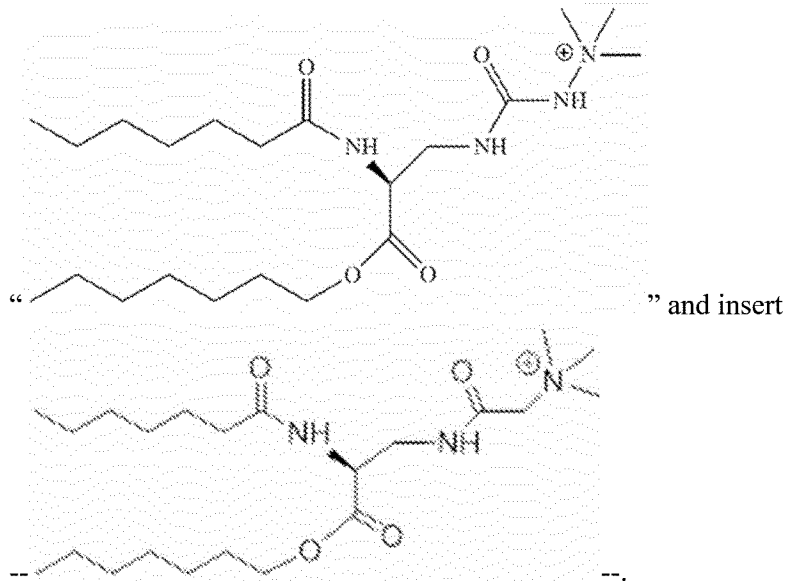" and insert -- --.